United States Patent
Yu et al.

(10) Patent No.: US 11,160,526 B2
(45) Date of Patent: Nov. 2, 2021

(54) METHOD AND APPARATUS FOR SCATTER ESTIMATION IN CONE-BEAM COMPUTED TOMOGRAPHY

(71) Applicant: Accuray, Inc., Sunnyvale, CA (US)

(72) Inventors: Zhicong Yu, Highland Hts., OH (US); Chuanyong Bai, Solon, OH (US); Amit Jain, Solon, OH (US); Daniel Gagnon, Twinsburg, OH (US)

(73) Assignee: Accuray, Inc., Sunnyvale, CA (US)

( * ) Notice: Subject to any disclaimer, the term of this patent is extended or adjusted under 35 U.S.C. 154(b) by 53 days.

(21) Appl. No.: 16/694,202

(22) Filed: Nov. 25, 2019

(65) Prior Publication Data

US 2020/0170600 A1 Jun. 4, 2020

Related U.S. Application Data

(60) Provisional application No. 62/773,712, filed on Nov. 30, 2018, provisional application No. 62/773,700, (Continued)

(51) Int. Cl.
*A61B 6/00* (2006.01)
*G06T 11/00* (2006.01)
(Continued)

(52) U.S. Cl.
CPC ............ *A61B 6/5282* (2013.01); *A61B 6/027* (2013.01); *A61B 6/032* (2013.01); *A61B 6/06* (2013.01);
(Continued)

(58) Field of Classification Search
CPC .................................................. A61B 6/5282
See application file for complete search history.

(56) References Cited

U.S. PATENT DOCUMENTS 4,190,773 A * 2/1980 Braden ................ A61B 6/032
378/10
5,615,279 A 3/1997 Yoshioka et al.
(Continued)

FOREIGN PATENT DOCUMENTS

DE  10 2006 007058 A1  7/2007
EP     1062914 A1    12/2000
(Continued)

OTHER PUBLICATIONS

International Search Report and Written Opinion from PCT/US2019/063080 dated Mar. 16, 2020.
(Continued)

*Primary Examiner* — Chih-Cheng Kao
(74) *Attorney, Agent, or Firm* — Calfee, Halter & Griswold LLP

(57) ABSTRACT

An x-ray imaging apparatus and associated methods are provided to receive measured projection data in a primary region and measured scatter data in a shadow region and determine an estimated scatter in the primary region during a current rotation based on the measured scatter data in the shadow region from a neighboring rotation. Coverage of the shadow region during the neighboring rotation overlaps the primary region during the current rotation. A beamformer is configured to adjust a shape of the radiation beam to create the primary and shadow regions on the detector, including an embodiment to follow the Tam-Danielson window during a helical scan.

20 Claims, 14 Drawing Sheets

Related U.S. Application Data filed on Nov. 30, 2018, provisional application No. 62/796,831, filed on Jan. 25, 2019, provisional application No. 62/800,287, filed on Feb. 1, 2019, provisional application No. 62/801,260, filed on Feb. 5, 2019, provisional application No. 62/813,335, filed on Mar. 4, 2019, provisional application No. 62/821,116, filed on Mar. 20, 2019, provisional application No. 62/836,357, filed on Apr. 19, 2019, provisional application No. 62/836,352, filed on Apr. 19, 2019, provisional application No. 62/843,796, filed on May 6, 2019, provisional application No. 62/878,364, filed on Jul. 25, 2019.

(51) Int. Cl.
| | | |
|---|---|---|
| *A61B 6/03* | (2006.01) | |
| *A61B 6/06* | (2006.01) | |
| *A61B 6/02* | (2006.01) | |
| *A61N 5/10* | (2006.01) | |
| *A61B 6/04* | (2006.01) | |
| *A61B 6/08* | (2006.01) | |
| *G06T 7/30* | (2017.01) | |
| *A61B 5/055* | (2006.01) | |

(52) U.S. Cl.
CPC .......... *A61B 6/405* (2013.01); *A61B 6/4078* (2013.01); *A61B 6/4085* (2013.01); *A61B 6/469* (2013.01); *A61B 6/488* (2013.01); *A61B 6/5205* (2013.01); *G06T 11/005* (2013.01); *A61B 5/055* (2013.01); *A61B 6/025* (2013.01); *A61B 6/03* (2013.01); *A61B 6/035* (2013.01); *A61B 6/0407* (2013.01); *A61B 6/08* (2013.01); *A61B 6/4014* (2013.01); *A61B 6/4021* (2013.01); *A61B 6/4028* (2013.01); *A61B 6/4064* (2013.01); *A61B 6/4435* (2013.01); *A61B 6/4441* (2013.01); *A61B 6/4458* (2013.01); *A61B 6/481* (2013.01); *A61B 6/482* (2013.01); *A61B 6/483* (2013.01); *A61B 6/484* (2013.01); *A61B 6/541* (2013.01); *A61B 6/582* (2013.01); *A61N 5/107* (2013.01); *A61N 5/1049* (2013.01); *A61N 5/1067* (2013.01); *A61N 5/1071* (2013.01); *A61N 5/1082* (2013.01); *A61N 2005/1085* (2013.01); *A61N 2005/1091* (2013.01); *A61N 2005/1095* (2013.01); *G06T 7/30* (2017.01); *G06T 11/008* (2013.01); *G06T 2207/10081* (2013.01); *G06T 2210/41* (2013.01); *G06T 2211/404* (2013.01); *G06T 2211/412* (2013.01); *G06T 2211/424* (2013.01); *G06T 2211/428* (2013.01); *G06T 2211/432* (2013.01)

(56) References Cited

U.S. PATENT DOCUMENTS

| | | | |
|---|---|---|---|
| 6,233,478 B1* | 5/2001 | Liu | A61B 6/541 |
| | | | 378/8 |
| 6,307,909 B1 | 10/2001 | Flohr et al. | |
| 7,050,528 B2 | 5/2006 | Chen | |
| 7,660,380 B2 | 2/2010 | Boese et al. | |
| 8,116,430 B1 | 2/2012 | Shapiro et al. | |
| 8,467,497 B2 | 6/2013 | Lu et al. | |
| 8,588,363 B2 | 11/2013 | Flohr | |
| 9,400,332 B2 | 7/2016 | Star-Lack et al. | |
| 2003/0076927 A1 | 4/2003 | Shigeyuki et al. | |
| 2004/0091079 A1 | 5/2004 | Zapalac | |
| 2004/0202360 A1* | 10/2004 | Besson | A61B 6/5282 |
| | | | 382/131 |
| 2005/0053188 A1* | 3/2005 | Gohno | A61B 6/032 |
| | | | 378/15 |
| 2005/0251029 A1 | 11/2005 | Khamene et al. | |
| 2006/0109954 A1 | 5/2006 | Gohno | |
| 2006/0262894 A1 | 11/2006 | Bernhadt et al. | |
| 2007/0127621 A1 | 6/2007 | Grass et al. | |
| 2007/0189444 A1 | 8/2007 | Van Steven-Daal et al. | |
| 2008/0112532 A1 | 5/2008 | Schlomka et al. | |
| 2009/0080603 A1 | 3/2009 | Shukla et al. | |
| 2009/0135994 A1 | 5/2009 | Yu et al. | |
| 2009/0161826 A1 | 6/2009 | Gertner et al. | |
| 2009/0225932 A1 | 9/2009 | Zhu et al. | |
| 2009/0283682 A1 | 11/2009 | Star-Lack et al. | |
| 2010/0046819 A1* | 2/2010 | Noo | A61B 6/027 |
| | | | 382/131 |
| 2010/0208964 A1 | 8/2010 | Wiegert et al. | |
| 2011/0142312 A1 | 6/2011 | Toth et al. | |
| 2012/0014582 A1 | 1/2012 | Schaefer et al. | |
| 2012/0207370 A1* | 8/2012 | Fahimian | A61B 6/484 |
| | | | 382/131 |
| 2012/0263360 A1 | 10/2012 | Zhu et al. | |
| 2012/0294504 A1 | 11/2012 | Kyriakou | |
| 2013/0101082 A1 | 4/2013 | Jordan et al. | |
| 2013/0294570 A1 | 11/2013 | Hansis | |
| 2014/0018671 A1 | 1/2014 | Li et al. | |
| 2014/0086383 A1 | 3/2014 | Huwer et al. | |
| 2015/0297165 A1 | 10/2015 | Tanaka et al. | |
| 2015/0305696 A1 | 10/2015 | Yamakawa et al. | |
| 2016/0016009 A1 | 1/2016 | Manzke et al. | |
| 2016/0120486 A1 | 5/2016 | Goto et al. | |
| 2016/0262709 A1 | 9/2016 | Siewerdsen et al. | |
| 2017/0000428 A1 | 1/2017 | Goto | |
| 2017/0197098 A1 | 7/2017 | Hirasawa et al. | |
| 2017/0205360 A1* | 7/2017 | Cinquin | A61B 6/582 |
| 2017/0332982 A1* | 11/2017 | Koehler | A61B 6/5241 |
| 2018/0070894 A1 | 3/2018 | Osaki et al. | |
| 2018/0192978 A1 | 7/2018 | Naylor | |
| 2018/0345042 A1 | 12/2018 | Voronenko et al. | |
| 2019/0099149 A1 | 4/2019 | Li | |
| 2020/0016432 A1 | 1/2020 | Maolinbay | |
| 2020/0121267 A1 | 4/2020 | Deutschmann | |
| 2020/0402644 A1 | 12/2020 | Zhou et al. | |
| 2021/0165122 A1 | 6/2021 | Morton | |

FOREIGN PATENT DOCUMENTS

| | | |
|---|---|---|
| EP | 2383702 A1 | 11/2011 |
| JP | H09 218939 A | 8/1997 |
| JP | 2004 136021 | 5/2004 |
| JP | 2008 036275 | 2/2008 |
| WO | 2005/112753 A2 | 12/2005 |
| WO | 2006/078386 A2 | 7/2006 |
| WO | 2010/014288 A1 | 2/2010 |
| WO | 2010/099621 A1 | 9/2010 |
| WO | 2015103184 A1 | 7/2015 |
| WO | 2018/156968 A1 | 8/2018 |
| WO | 2018/183748 A1 | 10/2018 |

OTHER PUBLICATIONS

International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063078 dated Oct. 8, 2020.
International Search Report and Written Opinion from PCT/US2019/063083 dated Mar. 16, 2020.
International Search Report and Written Opinion from PCT/US2019/063085 dated Mar. 16, 2020.
Invitation to Pay Additional Fees from PCT/US2019/063086 dated Mar. 26, 2020.
International Search Report and Written Opinion from PCT/US2019/063087 dated Apr. 3, 2020.
International Search Report and Written Opinion from PCT/US2019/063077 dated Mar. 16, 2020.

(56) References Cited

OTHER PUBLICATIONS

International Search Report and Written Opinion from PCT/US2019/063076 dated Mar. 16, 2020.
International Search Report and Written Opinion from PCT/US2019/063074 dated Mar. 23, 2020.
International Search Report and Written Opinion from PCT/US2019/063086 dated Nov. 16, 2020.
Kang et al., "Accurate for Head and Neck Cancer Patients Using 2D and 3D Image Guidance", Journal of Applied Clinical Medical Physics, vol. 12, No. 1, Dec. 1, 2011, pp. 86-96, XP055734549.
Ramamurthi et al., "Region of Interest Cone Beam Tomography With Prior CT Data," Conference Record of the 37th Asilomar Conference on Signals, Systems, & Computers, vol. 2, Nov. 9, 2003, pp. 1924-1927.
Spearman, et al. Effect of Automated Attenuation-Based Tube Voltage Selection on Radiation Dose at CT: An Observational Study on a Global Scale11 , Radiology, vol. 279, No. Apr. 1, 2016 (Apr. 1, 2016), pp. 167-174, XP055734550.
Vinson et al., "X-Ray Micro-CT With a Displaced Detector Array: Application to Helical Cone-Beam Reconstruction," Medical Physics, vol. 30, No. 10, Oct. 1, 2003, pp. 2758-2761.
Wang et al., "A General Cone-Beam Reconstruction Algorithm," IEEE Transactions on Medical Imaging, vol. 12, No. 3, Sep. 1, 1993.
Wang, "X-Ray Micro-CT With a Displaced Detector Array," Medical Physics, vol. 29, No. 7, Jul. 1, 2002.
Office Action from U.S. Appl. No. 16/694,145 dated Mar. 17, 2021, 10 pages.
Office Action from U.S. Appl. No. 16/694,190 dated Mar. 26, 2021, 9 pages.
Notice of Allowance from U.S. Appl. No. 16/694,190 dated Jun. 23, 2021, 8 pages.
Office Action from U.S. Appl. No. 16/694,230 dated Apr. 1, 2021, 6 pages.
Office Action from U.S. Appl. No. 16/694,192 dated Jun. 10, 2021, 10 pages.
Office Action from U.S. Appl. No. 16/694,218 dated Apr. 15, 2021, 7 pages.
Restriction Requirement from U.S. Appl. No. 16/694,210 dated Jun. 10, 2021, 6 pages.
Clackdoyle, et al., Data consistency conditions for truncated fanbeam and parallel projections, Med. Phys. Feb. 2015, pp. 831-845, vol. 42, No. 2.
Defrise, et al., A solution to the long-object problem in helical cone-beam tomography, Physics in Medicine and Biology, 2000, pp. 623-643, vol. 45.
Hsieh, et al., A novel reconstruction algorithm to extend the CT scan field-of-view, Med. Phys., Sep. 2004, pp. 2385-2391, vol. 31, No. 9.
Katsevich, A., An improved exact filtered backprojection algorithm for spiral computed tomography, Advances in Applied Mathematics, 2004, pp. 691-697, vol. 32.
Kudo et al., Exact and approximate algorithms for helical cone-beam CT, Physics in Medicine and Biology, 2004, pp. 1-26, vol. 49, No. 13.
Kunze, et al., Cone beam reconstruction with displaced flat panel detector, 10th International Meeting on Fully Three-Dimensional Image Reconstruction in Radiology and Nuclear Medicine, 2009, pp. 138-141.
Li et al., Scatter kernel estimation with an edge-spread function method for cone-beam computed tomography imaging, Physics in Medicine and Biology, pp. 6729-6748, vol. 51, 2008.
Maslowski, et al., Acuros CTS: A fast, linear Boltzmann transport equation solver for computed tomography scatter—Part I: Core algorithms and validation, Med. Phys., 2018, pp. 1-15.
Ning, et al., X-ray scatter correction algorithm for cone beam CT imaging, Med. Phys., May 2004, pp. 1195-1202, vol. 31, No. 5.
Noo et al., A new scheme for view-dependent data differentiation in fan-beam and cone-beam computed tomography, Physics in Medicine and Biology, 2007, pp. 5593-5414, vol. 52.
Schäfer, et al., FBP and BPF reconstruction methods for circular X-ray tomography with off-center detector, Med. Phys., Jul. 2011, pp. S85-S94, vol. 38, No. 7.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Siewerdsen, et al., A simple, direct method for x-ray scatter estimation and correction in digital radiography and cone-beam CT, Med. Phys., Jan. 2006, pp. 187-197, vol. 33, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Yu, et al., Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions on Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
Zhu, et al. Noise suppression in scatter correction for cone-beam CT, American Association of Physicists in Medicine, 2009, pp. 741-752, vol. 36, No. 3.
Office Action from U.S. Appl. No. 16/694,161 dated Sep. 13, 2021, 18 pages.

* cited by examiner

METHOD AND APPARATUS FOR SCATTER ESTIMATION IN CONE-BEAM COMPUTED TOMOGRAPHY

CROSS-REFERENCE TO RELATED APPLICATIONS

This application claims the benefit of eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on the same day, including, entitled "MULTIMODAL RADIATION APPARATUS AND METHODS;" entitled "APPARATUS AND METHODS FOR SCALABLE FIELD OF VIEW IMAGING USING A MULTI-SOURCE SYSTEM;" entitled "INTEGRATED HELICAL FAN-BEAM COMPUTED TOMOGRAPHY IN IMAGE-GUIDED RADIATION TREATMENT DEVICE;" entitled "COMPUTED TOMOGRAPHY SYSTEM AND METHOD FOR IMAGE IMPROVEMENT USING PRIOR IMAGE;" entitled "OPTIMIZED SCANNING METHODS AND TOMOGRAPHY SYSTEM USING REGION OF INTEREST DATA;" entitled "HELICAL CONE-BEAM COMPUTED TOMOGRAPHY IMAGING WITH AN OFF-CENTERED DETECTOR;" entitled "MULTI-PASS COMPUTED TOMOGRAPHY SCANS FOR IMPROVED WORKFLOW AND PERFORMANCE;" entitled "ASYMMETRIC SCATTER FITTING FOR OPTIMAL PANEL READOUT IN CONE-BEAM COMPUTED TOMOGRAPHY;" entitled "METHOD AND APPARATUS FOR IMPROVING SCATTER ESTIMATION AND CORRECTION IN IMAGING;" and entitled "METHOD AND APPARATUS FOR IMAGE RECONSTRUCTION AND CORRECTION USING INTER-FRACTIONAL INFORMATION." The contents of all above-identified patent application(s) and patent(s) are fully incorporated herein by reference.

FIELD OF THE INVENTION

Aspects of the disclosed technology relate to estimating scatter in imaging projection data, and, more particularly, to an apparatus and method utilizing shadow region data to estimate scatter in primary region projection data, including during cone-beam computed tomography (CT) scans.

BACKGROUND

Scatter in cone-beam CT can account for a significant portion of the detected photons when no anti-scatter grids are used with a wide collimation opening. Scatter can negatively impact image quality, including contrast and quantitative accuracy. Consequently, scatter measurement and scatter correction are applicable to cone-beam CT data processing and image reconstruction, including in the context of image-guided radiation treatment (IGRT). IGRT can make use of medical imaging technology, such as CT, to collect images of a patient before, during, and/or after treatment.

Most scatter measurement and correction approaches fall into the following categories. In the first category are the model-based methods. These methods model both a data acquisition system and the interaction process between x-rays and materials. The former requires detailed knowledge of the major components of the entire imaging chain as well as information of the patient, which may be obtained from a planning CT or a first-pass reconstruction without scatter correction. These methods can either be realized stochastically (e.g., Monte-Carlo-simulation based approaches) or deterministically (e.g., radiative-transfer-equation based approaches). The former can be computationally costly, and the latter is generally considered as an open problem in the field. The model-based methods are typically patient specific and more accurate. However, these methods require a considerable amount of prior information on the data acquisition system and the patient, such that the effectiveness of these methods is highly dependent on the modeling accuracy. Furthermore, they are also highly demanding in terms of computational power and time resulting in a significant negative impact on workflow and throughput.

In the second category are the deconvolution-kernel based methods. Measured x-ray projection data are considered a convolution result of the primary and the scatter kernels. These methods perform a deconvolution process to separate the primary and scatter by using appropriate kernels that are established ahead of time. These methods are practical and effective to a certain extent. However, they are sensitive to the kernel design, especially in terms of material and shape of the scanned object.

In the third category are the direct-measurement based methods, such as beam-stopper-array and primary modulation. These methods are capable of measuring scatter while acquiring projection data. They do not require prior information, and thus are very robust and practical. Drawbacks of such methods include wasted dose and/or degraded image quality.

Another direct-measurement based method measures scatter from a shadowed region of the detector in the longitudinal direction, which is then further used for estimation of the scatter located inside the collimation opening (primary region). However, this method is designed for a single circular scan (i.e., measurements in the primary and scatter regions occur concurrently during the same rotation), requires detector availability outside on both sides (in the longitudinal direction) of the collimation opening, and is limited in terms of estimation accuracy.

BRIEF SUMMARY

In one embodiment, an imaging apparatus includes a rotating x-ray source for emitting a radiation beam, an x-ray detector positioned to receive radiation from the x-ray source, a beamformer configured to adjust a shape of the radiation beam emitted by the x-ray source, such that a primary region of the x-ray detector is directly exposed to the radiation beam and at least one shadow region of the x-ray detector is blocked from direct exposure to the radiation beam by the beamformer, and a data processing system configured to receive measured projection data in the primary region and measured scatter data in the at least one shadow region and determine an estimated scatter in the primary region during a current rotation based on the measured scatter data in the at least one shadow region during at least one of a previous rotation or a next rotation, where coverage of the at least one shadow region during at least one of the previous rotation or the next rotation overlaps the primary region during the current rotation.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Figure 1:
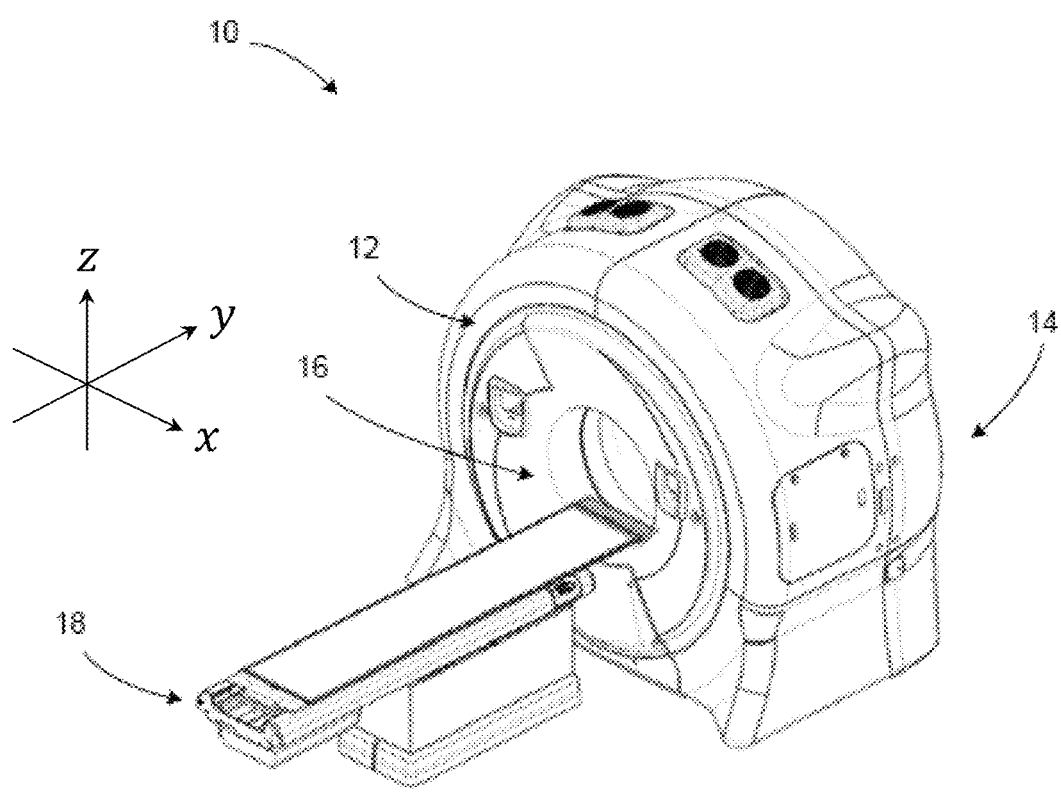
FIG. 1 is a perspective view of an exemplary x-ray imaging apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to estimating scatter in imaging projection data, including utilizing shadow region data to estimate scatter in primary region projection data during cone-beam CT scans. In some embodiments, a radiotherapy delivery device and method can make use of an integrated low-energy radiation source for CT for use in conjunction with or as part of IGRT. In particular, for example, a radiotherapy delivery device and method can combine a low-energy collimated radiation source for imaging in a gantry using rotational (e.g., helical or step-and-shoot) image acquisition along with a high-energy radiation source for therapeutic treatment.

The low-energy radiation source (e.g., kilovolt (kV)) can produce higher quality images than via use of the high-energy radiation source (e.g., megavolt (MV)) for imaging. Images generated with kV energy typically have better tissue contrast than with MV energy. High quality volume imaging is needed for visualization of targets and organs-at-risk (OARS), for adaptive therapy monitoring and for treatment planning/re-planning. In some embodiments, the kV imaging system can also be used for positioning, motion tracking, and/or characterization or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc.

In accordance with various embodiments, the x-ray imaging apparatus collimates a radiation source, including, for example, into a cone beam or a fan beam using, for example, a beamformer. In one embodiment, the collimated beam can be combined with a gantry that continuously rotates while the patient moves, resulting in a helical image acquisition.

In some embodiments, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high kV frame rates, and/or sparse data reconstruction techniques, to provide kV CT imaging on a radiation therapy delivery platform. Detectors (with various row/slice sizes, configurations, dynamic range, etc.), scan pitch, and/or dynamic collimation are additional features in various embodiments, including to selectively expose portions of the detector, as discussed in detail below. In particular, image quality can be improved (by estimating the scatter as described below) by using an adjustable beamformer/collimator on the x-ray (low-energy) imaging radiation source.

The imaging apparatus and method can provide selective and variable collimation of a radiation beam emitted by the source of radiation, including adjusting the radiation beam shape to expose less than the entire active area of an associated radiation detector (e.g., a radiation detector positioned to receive radiation from the x-ray radiation source). For example, a beamformer of the imaging apparatus can adjust the shape of the of the radiation beam as the pitch varies during a helical scan, including to capture the Tam-Danielson Window associated with the pitch, as discussed in detail below. Exposing only a primary region of the x-ray detector to direct radiation allows shadowed regions of the detector to receive only scatter. As discussed in detail below, scatter measurements in the shadow region of the detector can be used to estimate scatter in the primary region of the detector receiving projection data.

Figure 2:
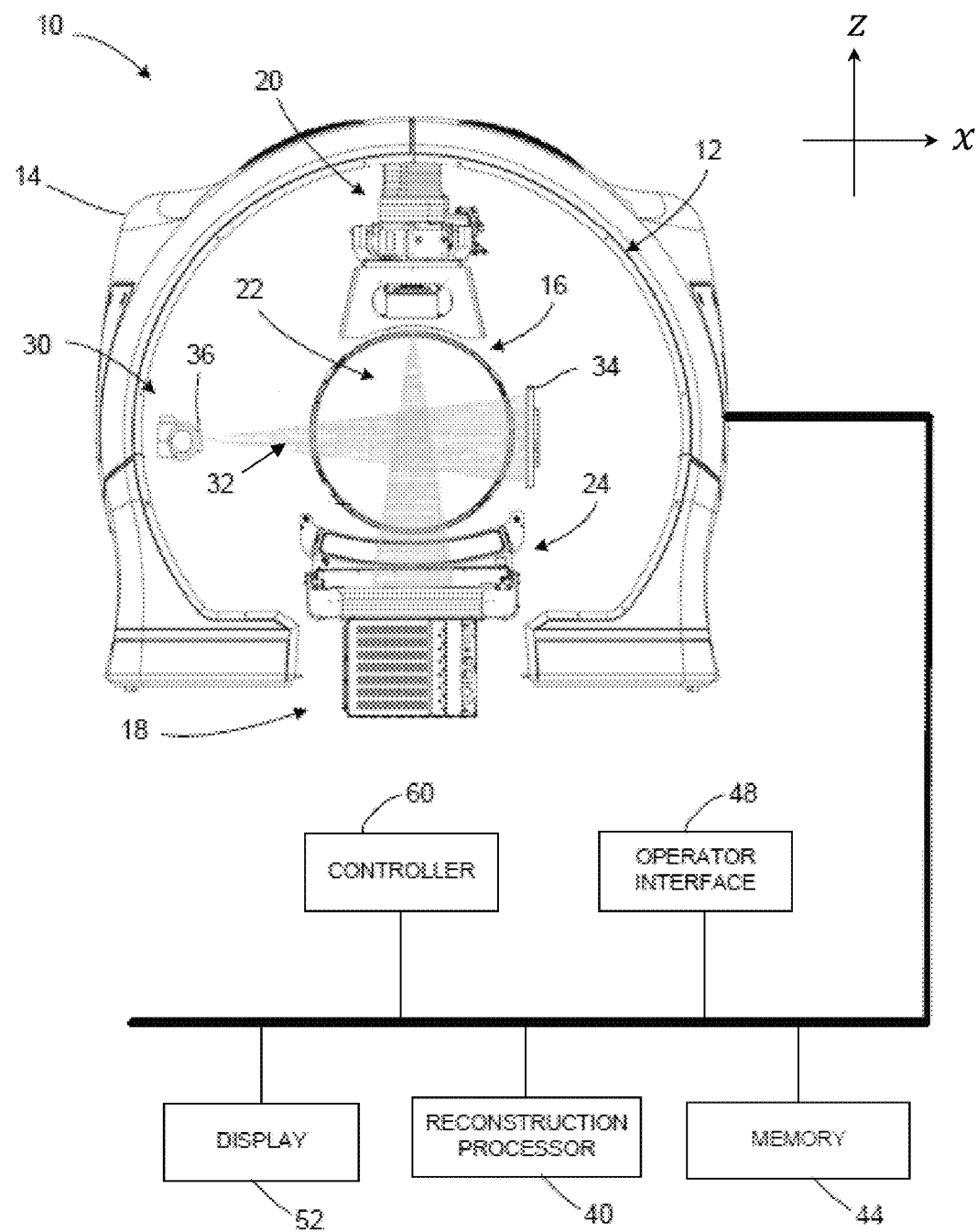
FIG. 2 is a diagrammatic illustration of an x-ray imaging apparatus integrated into an exemplary radiotherapy device in accordance with one aspect of the disclosed technology.

With reference to FIG. 1 and FIG. 2, an imaging apparatus 10 (e.g., an x-ray imaging apparatus) is shown. It will be appreciated that the imaging apparatus 10 may be associated with and/or integrated into a radiotherapy device (as shown in FIG. 2) that can be used for a variety of applications, including, but not limited to IGRT. The imaging apparatus 10 includes a rotatable gantry system, referred to as gantry 12 supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, kV and MV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of an imaging radiation source (e.g., x-ray) and an associated radiation detector while providing sufficient bandwidth for the high-quality imaging data received by the detector. A slip-ring gantry can eliminate gantry rotations in alternating directions in order to wind and unwind cables carrying the power and signals associated with the device. As is discussed more fully below, such a configuration will allow for continuous helical computed tomography, including cone beam CT (CBCT), even when integrated into an IGRT system.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. The patient support 18 can also be moved in a limited range up and down, left and right once it is in the bore 16 to adjust the patient position for optimal treatment. Axes x, y, and z are shown, where, viewing from the front of the gantry 12, the x-axis is horizontal and points to the right, the y-axis points into the gantry plane, and the z-axis is vertical and points to the top. The x-, y-, and z-axes follow the right-hand rule.

It will be appreciated that other variations can be employed without departing from the scope of the disclosed technology. For example, the rotatable gantry 12 and patient support 18 can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The device 10 is capable of volume-based and planar-based imaging acquisitions. For example, in various embodiments, the device 10 may be used to acquire volume images and/or planar images and execute the associated processing methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) linear movement, speed, and/or trajectories, etc., and combinations thereof may be used, including in combination with the various embodiments of radiotherapy devices 10 described above.

As shown in FIG. 2, the x-ray imaging apparatus 10 includes a source of imaging radiation 30 coupled to or otherwise supported by the rotatable gantry 12. The source of imaging radiation 30 emits a radiation beam (indicated generally as 32) for generating high-quality images. In this embodiment, the source of imaging radiation is an x-ray source 30, configured as a kilovoltage (kV) source (e.g., a clinical x-ray source having an energy level in the range of about 20 kV to about 150 kV). In one embodiment, the kV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments.

The x-ray imaging apparatus 10 also can include another source of radiation 20 coupled to or otherwise supported by the rotatable gantry 12. In accordance with one embodiment, the source of radiation 20 is configured as a source of therapeutic radiation, such as a high-energy source of radiation used for treatment of a tumor within a patient in a region of interest. It will be appreciated that the source of therapeutic radiation can be a high-energy x-ray beam (e.g., megavoltage (MV) x-ray beam), and/or a high-energy particle beam (e.g., a beam of electrons, a beam of protons, or a beam of heavier ions, such as carbon) or another suitable form of high-energy radiation without departing from the scope of the disclosed technology. In one embodiment, the source of radiation 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the source of radiation 20 has a higher energy level (peak and/or average, etc.) than the source of imaging radiation 30.

In one embodiment, the source of radiation 20 is a LINAC producing therapeutic radiation (e.g., MV) and the imaging system comprises an independent source of imaging radiation 30 producing relatively low intensity and lower energy imaging radiation (e.g., kV). In other embodiments, the source of radiation 20 could be a radioisotope, such as, for example, Co-60, which can generally have energy>1 MeV. The source of radiation 20 can emit one or more beams of radiation (indicated generally by 22) toward a region-of-interest (ROI) within a patient supported on the patient support 18 in accordance with a treatment plan.

In some embodiments, sources of radiation 20, 30 may be used in conjunction with one another to provide higher quality and better utilized images. In other embodiments, at least one additional radiation source can be coupled to the rotatable gantry 12 and operated to acquire projection data at a peak photon energy distinct from the peak photon energies of sources of radiation 20, 30.

Although FIGS. 1 and 2 depict an x-ray imaging apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A detector 34 (e.g., two-dimensional flat detector or curved detector) can be coupled to or otherwise supported by the rotatable gantry 12. The x-ray detector 34 is positioned to receive radiation from the x-ray source 30 and can rotate along with the x-ray source 30. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the radiation source 30 rotates around and emits radiation toward the patient. It will be appreciated that the x-ray detector 34 can take on a number of configurations without departing from the scope of the disclosed technology. As illustrated in FIG. 2, the x-ray detector 34 can be configured as a flat-panel detector (e.g., a multi-row flat panel detector).

In accordance with another exemplary embodiment, the x-ray detector 34 can be configured as a curved detector.

A collimator or beamformer assembly (indicated generally as 36) is positioned relative to the imaging (x-ray) source 30 to selectively control and adjust a shape of a radiation beam 32 emitted by the x-ray source 30 to selectively expose a portion or region of the active area of the x-ray detector 34. The beamformer 36 can also control how the radiation beam 32 is positioned on the detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and translated.

As is discussed more fully below, the beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which will be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each scan rotation (e.g., using a pitch of 1), with about 1-2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra area. Various embodiments may include an optimization of the features that control selective exposure of the detector (e.g., beam size, collimation, pitch, detector data capture, etc.) such that the beam is thin enough for sufficient primary (exposed) and shadowed regions, but thick enough for speed and dosage control.

The beamformer 36 can be controlled such that the radiation beam 32 from the x-ray source 30 covers as much or as little of the x-ray detector 34 based on the particular imaging task and scatter estimation process being carried out. Generally, the beam can be controlled to yield radiation beams 32 that are of any shape and size that results in a sufficient primary region of the x-ray detector, which is directly exposed to the radiation beam, and at least one shadow region of the x-ray detector, which is blocked from direct exposure to the radiation beam by the beamformer.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

The beamformer may be configured in a variety of ways that allow it to adjust the shape of the radiation beam 32 emitted by the x-ray source 30. For example, the collimator 36 can be configured to include a set of jaws or other suitable members that define and selectively adjust the size of an aperture through which the radiation beam from the x-ray source 30 may pass in a collimated manner. In accordance with one exemplary configuration, the collimator 36 can include an upper jaw and a lower jaw, where the upper and lower jaws are movable in different directions (e.g., parallel directions) to adjust the size of the aperture through which the radiation beam from the x-ray source 30 passes, and also to adjust the beam 32 position relative to the patient to illuminate only the portion of the patient to be imaged for optimized imaging and minimized patient dose. For example, a collimator can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact absorbed by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a beamformer or collimator. The collimator/beamformer associated with the first source of radiation 20 can be configured in a number of ways, similar to the collimator 36 associated with the second source of radiation 30. The therapeutic radiation source 20 may be mounted, configured, and/or moved into the same plane or a different plane (offset) than the imaging source 30. In some embodiments, scatter caused by simultaneous activation of the radiation sources 20, 30 may be reduced by offsetting the radiation planes.

When integrated with a radiotherapy device, x-ray imaging apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, CT data, CBCT data, magnetic resonance imaging (MRI) data, positron emission tomography (PET) data or 3D rotational angiography (3DRA) data, and/or any information obtained from these or other imaging modalities. In some embodiments, the x-ray imaging apparatus 10 can track in-treatment patient, target, or ROI motion.

A reconstruction processor 40 can be operatively coupled to detector 24 and/or x-ray detector 34. In one embodiment, the reconstruction processor 40 is configured to generate patient images based on radiation received by detectors 24, 34 from the radiation sources 20, 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The x-ray imaging apparatus 10 can include an operator/user interface 48, where an operator of the x-ray imaging apparatus 10 can interact with or otherwise control the x-ray imaging apparatus 10 to provide input relating to scan or imaging parameters and the like. The operator interface 48 can include any suitable input devices, such as a keyboard, mouse, voice-activated controller, or the like. The x-ray imaging apparatus 10 can also include a display 52 or other human-readable element to provide output to the operator of the x-ray imaging apparatus 10. For example, the display 52 can allow the operator to observe reconstructed patient images and other information, such as imaging or scan parameters, related to operation of the x-ray imaging apparatus 10.

As shown in FIG. 2, the x-ray imaging apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer 36 controller, a controller coupled to the detector 24 and/or the detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, an x-ray imaging apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with an imaging apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with x-ray imaging apparatus 10.

X-ray imaging apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented.

Figure 3:
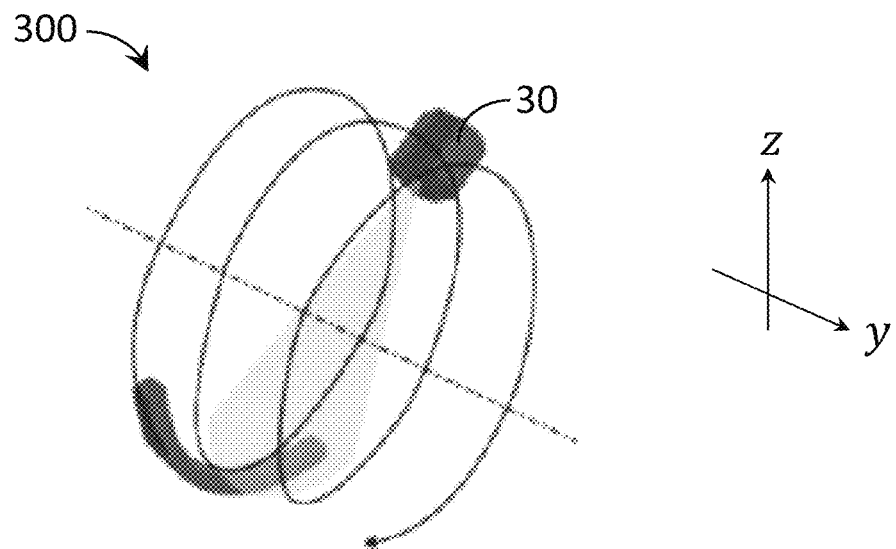
FIG. 3 is a diagrammatic illustration of an exemplary helical radiation source trajectory used in connection with aspects of the disclosed technology.
Figure 4:
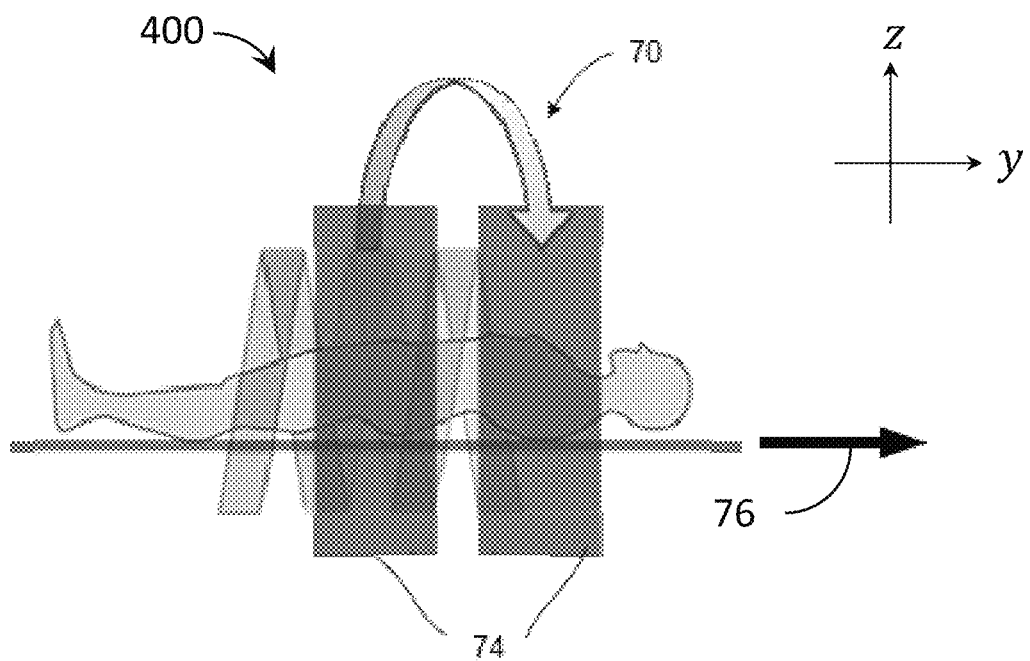
FIG. 4 is a diagrammatic illustration of an exemplary helical radiation source trajectory and collimation used in connection with aspects of the disclosed technology.

It will be appreciated that the x-ray source 30 and the x-ray detector 34 can be configured to provide rotation around the patient during an imaging scan in a number of ways. In one embodiment, synchronizing the motion and exposure of the x-ray source 30 with the longitudinal motion of the patient support 18 can provide a continuous helical acquisition of a patient image during a procedure. FIG. 3 provides an exemplary diagrammatic illustration of a helical source trajectory 300. In this embodiment, to achieve a helical trajectory, continuous circular rotation of the x-ray source 30 is combined with longitudinal movement of the patient. FIG. 4 provides an exemplary diagrammatic illustration of a helical image acquisition 400. The motion of the x-ray source 30 is indicated generally at 70, beamformer (e.g., 36) leaves are schematically indicated generally by 74, showing an exemplary beam column/slice width, and the patient support motion is indicated generally by the arrow 76 in the longitudinal direction (along the y-axis), as shown in FIG. 4.

In addition to continuous rotation of the radiation sources 20, 30 and detector(s) 24, 34 (e.g., continuous and constant rotation of the gantry with constant patient motion speed), it will be appreciated that other configurations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of radiotherapy devices 10 described above.

In one embodiment, the gantry 12 rotation speed, the patient support 18 speed, and the beamformer 36 shape could all be constant during image acquisition. In other embodiments, one or more of these variables could change dynamically during image acquisition. The gantry 12 rotation speed, patient support 18 speed, and/or beamformer 36 shape can be varied to balance different factors, including, for example, image quality and image acquisition time.

In other embodiments, these features can be combined with one or more other image-based activities or procedures, including, for example, patient set up, adaptive therapy monitoring, treatment planning, etc.

There are many determinants of image quality (e.g., X-ray source focal spot size, detector dynamic range, etc.). A limitation of kV CBCT image quality is scatter. Various approaches can be used to reduce scatter. One approach is to use an anti-scatter grid (which collimates the scatter). However, it can be problematic to implement a scatter grid on a kV imaging system, including for motion tracking and correction. Accurately estimating scatter in the projection data is necessary to improve the quality of the image data.

In various embodiments, scatter in the projection data acquired in a primary region of the detector 34 can be estimated by overlapping shadow regions of the detector 34 in neighboring rotations (previous or subsequent) with the current primary region and measuring the scatter in the shadowed/peripheral regions during these adjacent scans.

For example, FIG. 5A is a diagrammatic illustration of exemplary projections 500 onto a detector 502 during rotations of a helical trajectory scan 504. X-ray source 506 is shown with radiation beam 508 exposing a primary region 510 of the detector 502 to direct radiation. Detector 502 also has an active back region 512 and an active front region 514 that are shadowed from direct radiation by a beamformer (not shown). As shown in FIG. 5A, the scan includes exemplary previous, current, and next rotations from the series of rotations along the helical path 504 at the same azimuth angle projecting onto the same plane. Although not labeled, detector 502 includes the same primary region 510, back shadow region 512, and front shadow region 514 at each rotation (shaded sections).

Figure 5:
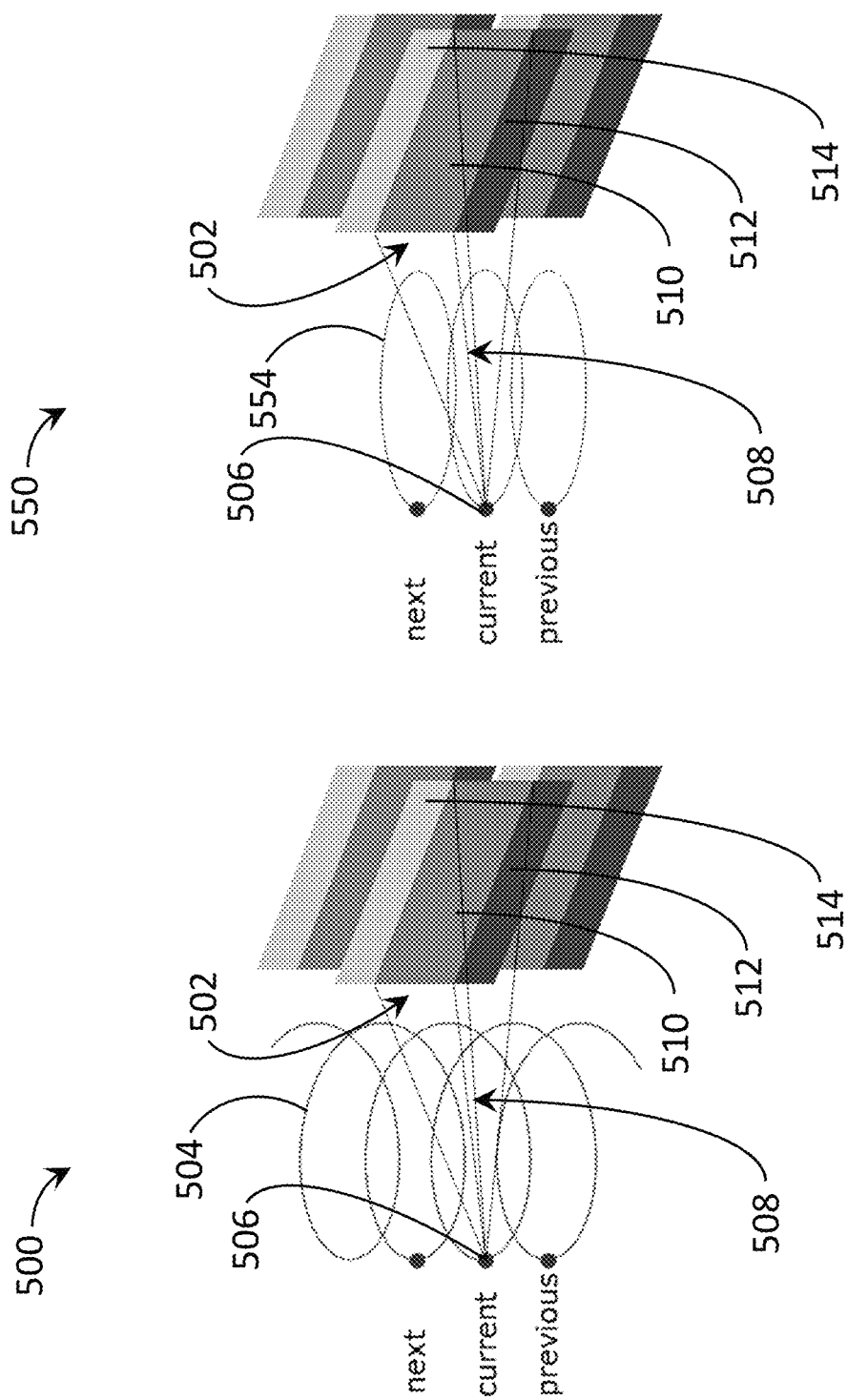
FIG. 5A is a diagrammatic illustration of exemplary projections onto a detector during rotations of a helical trajectory scan.
FIG. 5B is a diagrammatic illustration of exemplary projections onto a detector during successive circular rotations of a step-and-shoot scan.

As can be appreciated by the exemplary projections 500, the primary region 510 coverage of the current rotation overlaps with the front shadow region from the previous rotation and the back shadow region from the next rotation. In FIG. 5, the detector 502 associated with the current projection is shown offset from the detectors in the previous and next projections, however this is only to show the overlapping condition of the coverage.

In another example, FIG. 5B is a diagrammatic illustration of exemplary projections 550 onto detector 502 during successive circular rotations of a step-and-shoot scan 554. This type of scanning results in the same overlapping detector regions 510, 512, 514, during the exemplary previous, current, and next rotations from the series of rotations.

The primary region 510 and shadow regions 512, 514 can be controlled and adjusted by beamformer 36, as discussed above. Thus, the combination of multi-rotation scanning techniques (e.g., helical, step-and-shoot, etc.) and beamformer 36 capabilities supports the configurations shown in FIGS. 5A and 5B.

Scatter data acquired in these shadow regions during a previous or subsequent scan can be representative of the scatter in the primary region during the current scan with direct exposure because the overlapping target is essentially the same, albeit seen from a different rotation.

Figure 6:
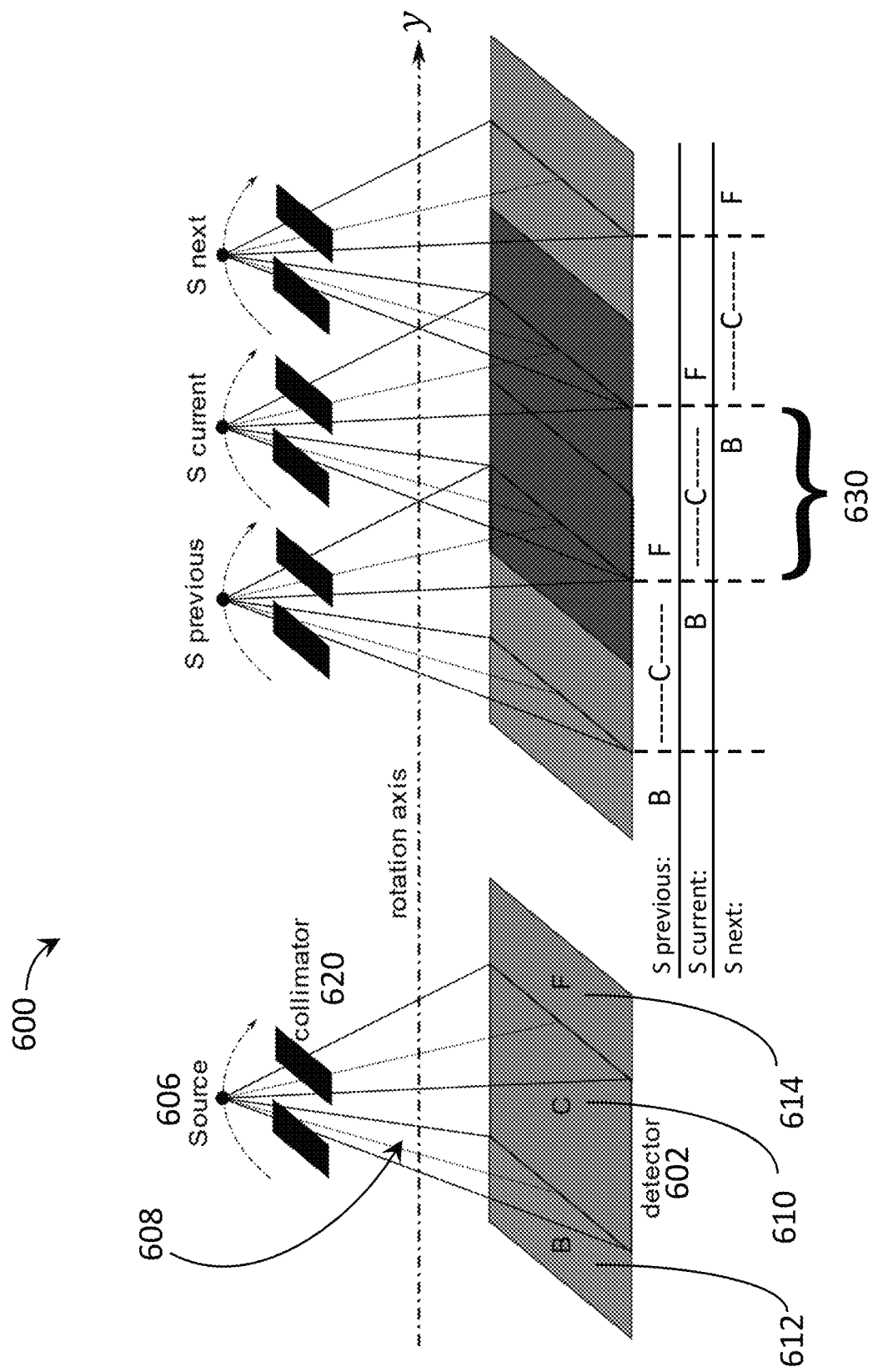
FIG. 6 is a diagrammatic illustration of exemplary projections onto an x-ray detector during successive rotations of a scan.

FIG. 6 is a diagrammatic illustration of exemplary projections 600 onto an x-ray detector 602 during successive rotations of a scan. On the left, rotating X-ray source 606 is shown emitting radiation beam 608 exposing a primary or center (C) region 610 of the detector 602 to direct radiation from X-ray source 606. Detector 602 also has an active back (B) shadow region 612 and an active front (F) shadow region 614 that are blocked from direct exposure to the radiation beam 608 by a beamformer/collimator 620. Beamformer/collimator 620 is configured to adjust a shape of the radiation beam 608 emitted by the x-ray source 606. The shadowed regions 612, 614 will only receive scattered radiation.

On the right, FIG. 6 shows a previous (S previous), current (S current), and next (S next) rotation along the scan path at the same azimuth angle projecting onto the same plane. Although not labeled, detector 602 includes the same primary or center (C) region 610, back (B) shadow region 612, and front (F) shadow region 614 during each rotation. The table below the exemplary projections shows how the shadow regions B, F overlap with the primary region C during successive rotations. As can be appreciated by the exemplary projections 600 and highlighted by exemplary coverage section 630, the primary region C coverage of the current rotation (S current) overlaps with the front shadow region F from the previous rotation (S previous) and the back shadow region B from the next rotation (S next). As discussed in detail below, this overlapping measurement data for each view can be used to estimate the scatter in the primary region C projection data.

Continued scan rotations result in the same or similar overlapping coverage. For example, on the next rotation, the current rotation (S current) will become the previous rotation (S previous) and the next rotation (S next) will become the current rotation (S current) and so on until the scan is complete. In this manner, primary region C and shadow region B and/or F measurement data can be made available for each view (except for possibly the first and last rotation, which may have one-sided shadow region data).

With continued reference to FIG. 6, each collimation opening is configured in such a way that the back (B) end 612 and the front (F) end 614 of the detector 602 in the axial or longitudinal direction (along the patient table (y-axis) direction) are not illuminated with direct radiation 608. These back (B) 612 (in the negative longitudinal direction along the rotation axis) and front (F) 614 (in the positive longitudinal direction along the rotation axis) shadow regions are designed for scatter measurement since they do not receive direct radiation. The primary or center (C) region 610 receives both direct projections and scatter.

In this manner, the scatter in the central region 610 of the current view can be estimated not only by the scatter measured at the current view, but also the scatter measured from the neighboring rotations (previous and/or next) that have the same/similar azimuth view angles. The data acquisition configuration is combined with scan geometry design to optimize the scatter measurement.

A data processing system (e.g., processor 40) can be configured to receive measured projection data in the primary region 610 and measured scatter data in at least one shadow region 612, 614, then determine an estimated scatter in the primary region 610 during a current rotation based on the measured scatter data in at least one shadow region 612, 614 during a previous and/or next rotation, when coverage of the shadow region 612, 614 during the previous or next rotation overlaps the primary region 610 during the current rotation, as shown in FIGS. 5 and 6. In one embodiment, determining the estimated scatter in the primary region 610 during the current rotation can also be based on the measured scatter data in at least one shadow region 612, 614 during the current rotation.

In one embodiment, the apparatus configuration and scan design can implement scatter correction in three steps: (1) Data acquisition: For each rotation, acquire projection data (primary+scatter) using the central (C) region of the detector 610 and measure scatter using the front (F) and back (B) shadow regions 614, 612 of the detector 602; (2) Scatter estimation: For each rotation, estimate the scatter component of the projection data from the central (C) region using both the scatter measurement of the current rotation and that of the neighboring rotations at the same azimuth angle; and (3) Scatter correction: Scatter estimated from step (2) is subtracted from the projection data to obtain scatter corrected projection data. The embodiments shown in FIGS. 5-6 represent helical (FIGS. 5A and 6) and circular (FIGS. 5B and 6) scans with two-sided shadow zones. One-sided embodiments will be discussed below.

Various techniques and methods can utilize different scan geometries, detector positioning, and/or beamformer window shapes. The detector 602 may also be offset in the transverse direction.

Figure 7:
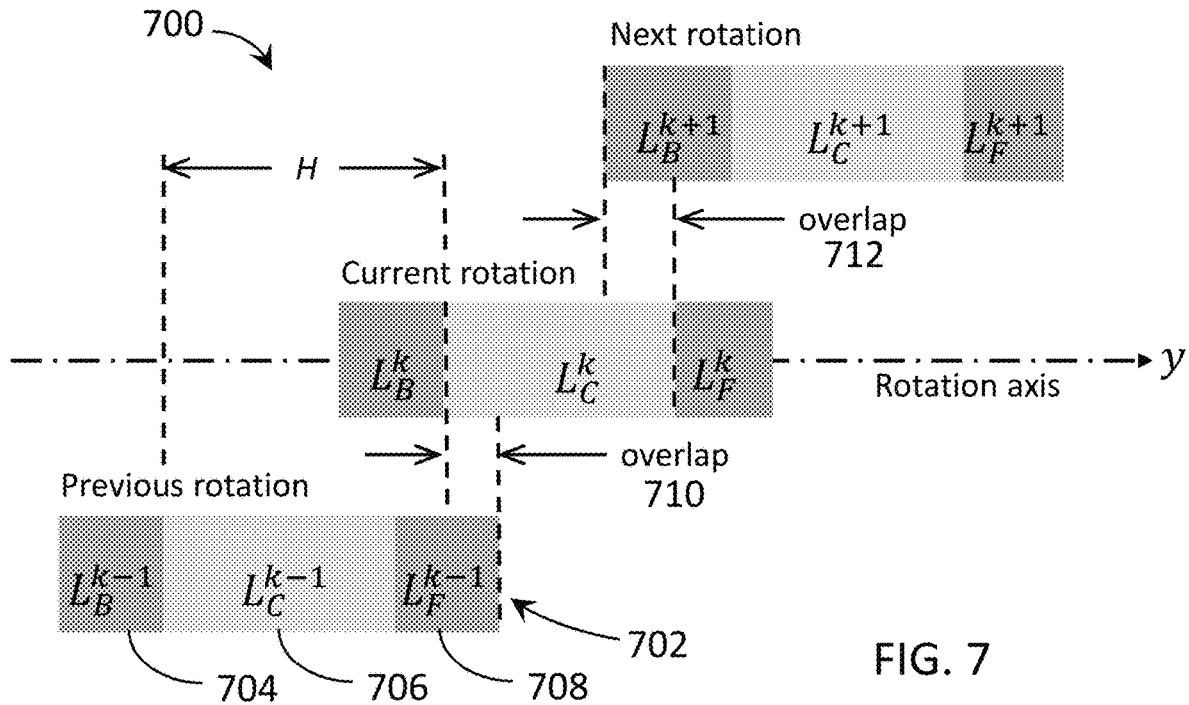
FIG. 7 shows schematic views of an exemplary detector with two-sided shadow regions during successive rotations of a scan.
Figure 8:
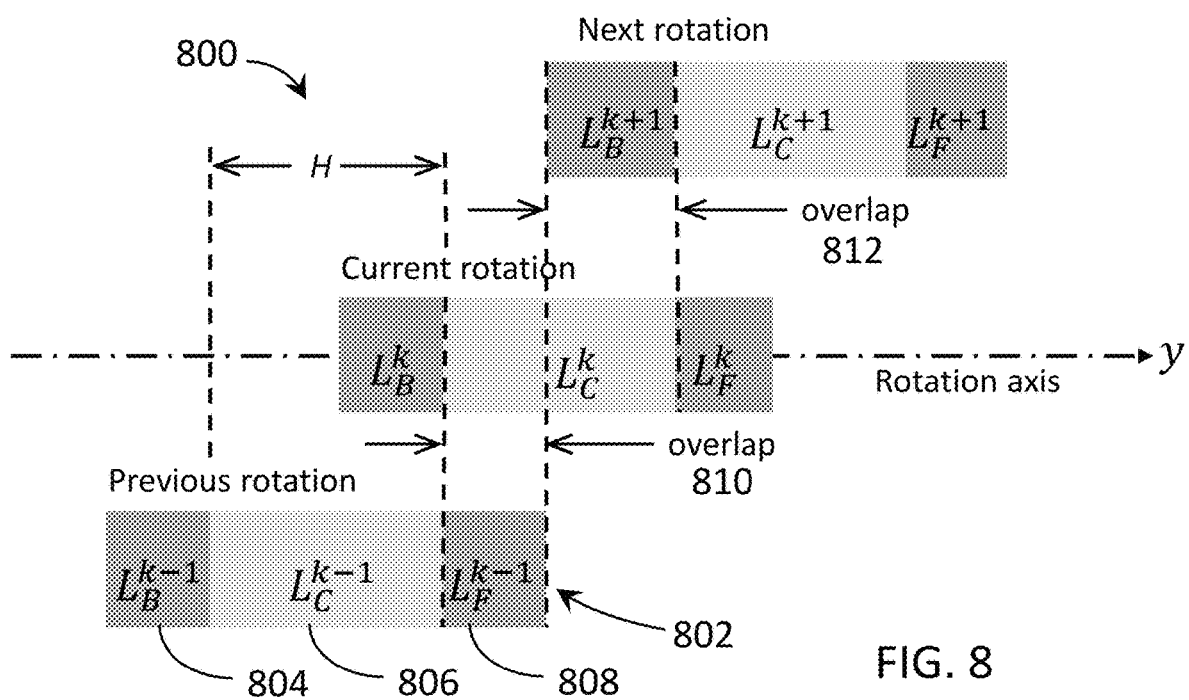
FIG. 8 shows schematic views of another exemplary detector with two-sided shadow regions during successive rotations of a scan.

FIGS. 7-8 show schematic views of exemplary detectors during scan geometries with two-sided shadow zones. For convenience, the following notation is used to identify the detector regions: let $L_B^k$, $L_C^k$, and $L_F^k$ be the axial length of the back shadow region, the central region, and the front-shadow region of the detector at the isocenter for the kth rotation, respectively; and let H be the traveled distance along the axial direction per rotation of the helical or step-and-shoot scans.

For scatter estimation, it is recommended that H satisfies the following condition:

$$H < \max(L_F, L_B) + L_C \quad (1)$$

If H satisfies this condition, there will be measured scatter from the neighboring rotations that can directly contribute to the scatter estimation of the current projection. Otherwise, scatter estimation of the current view can be obtained by interpolating in the axial direction between the back and front shadows, which is less accurate and robust.

For example, FIG. 7 shows schematic views of an exemplary detector 702 during scan geometry 700 with two-sided shadow regions during successive rotations of a scan. In particular, detector 702 includes a back shadow region 704 with axial length $L_B$, central (primary) region 706 with axial length $L_C$, and front shadow region 708 with axial length $L_F$. The detector 702 is shown with views during three successive rotations, where k is the current rotation, k−1 is the previous rotation, and k+1 is the next rotation.

As shown in FIG. 7, $H < L_F + L_C$, satisfying condition (1) above. If condition (1) is satisfied, at least one shadow region 704, 708 from a neighboring rotation (k−1 and/or k+1) will overlap coverage with the central region 706 during the current rotation (k). Here, a portion of the front shadow region 708 from the previous rotation (k−1) overlaps with the central region 706 during the current rotation (k), shown as overlap 710, and a portion of the back shadow region 704 from the next rotation (k+1) overlaps with the central region 706 during the current rotation (k), shown as overlap 712. The scatter measurements from these shadow regions 704, 708 can be used for estimating the scatter in the measured projection data in the central region 706, as described above.

Assuming that H satisfies the above condition (1), scatter measurements from neighboring rotations that overlap with the current measured projection data can be used to estimate the scatter of the current view.

For relatively small values of H, the shadow regions of more than one neighboring rotation on the same side may be available for scatter estimation.

An exemplary optimized balance between scan speed and accuracy of scatter estimation can be defined by the following condition:

$$H = L_C = L_F + L_B \quad (2)$$

For example, FIG. 8 shows schematic views of an exemplary detector 802 during scan geometry 800 with two-sided shadow regions during successive rotations of a scan. In particular, detector 802 includes a back shadow region 804 with axial length $L_B$, central (primary) region 806 with axial length $L_C$, and front shadow region 808 with axial length $L_F$. The detector 802 is shown with views during three successive rotations, where k is the current rotation, k−1 is the previous rotation, and k+1 is the next rotation.

As shown in FIG. 8, $H = L_C = L_F + L_B$, satisfying condition (2) above. If condition (2) is satisfied, the combined shadow regions 808 (previous), 804 (next) from neighboring rotations (k−1 and k+1) will completely overlap coverage with the central region 806 during the current rotation (k). In particular, the front shadow region 808 from the previous rotation (k−1) overlaps with the central region 806 during the current rotation (k), shown as overlap 810, and the back shadow region 804 from the next rotation (k+1) overlaps with the central region 806 during the current rotation (k), shown as overlap 812. The scatter measurements from these shadow regions 804, 808 can be used for estimating the scatter in the measured projection data in the central region 806, as described above. Overlap areas 810 and 812 provide complete coverage for central region 806, since $L_C = L_F + L_B$, which results in high accuracy of the scatter estimation. In addition, since $H=L_C$, the scan geometry optimizes speed by not overlapping the central region in successive rotations.

Figure 9:
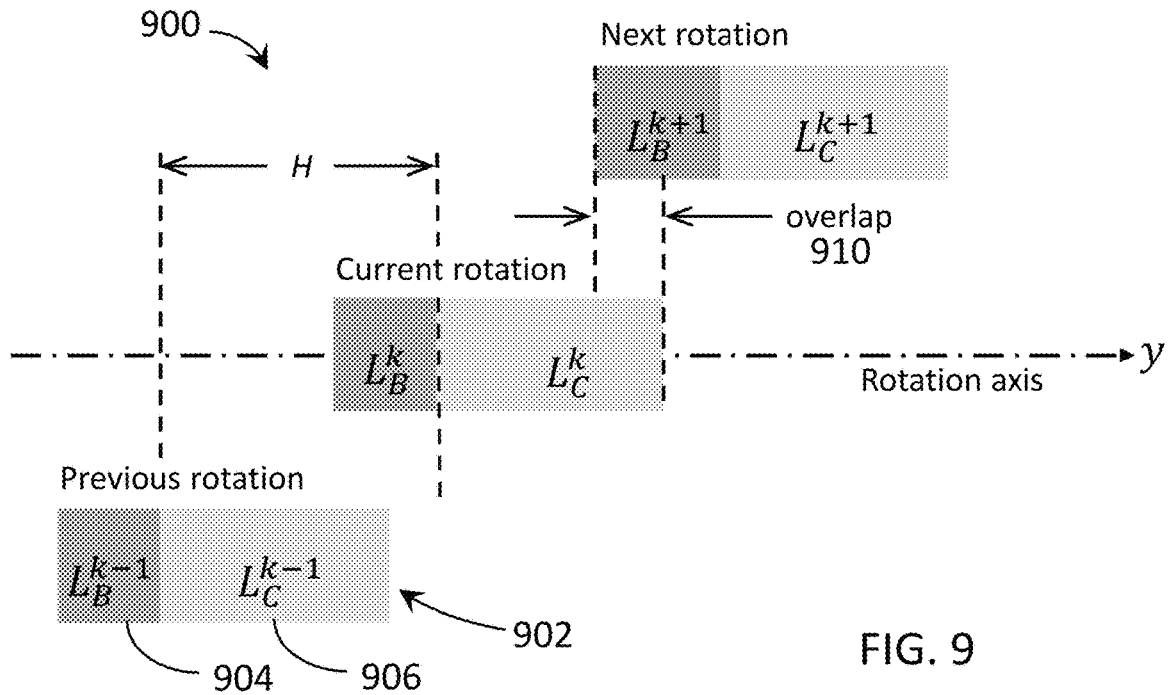
FIG. 9 shows schematic views of an exemplary detector with a one-sided shadow region during successive rotations of a scan.
Figure 10:
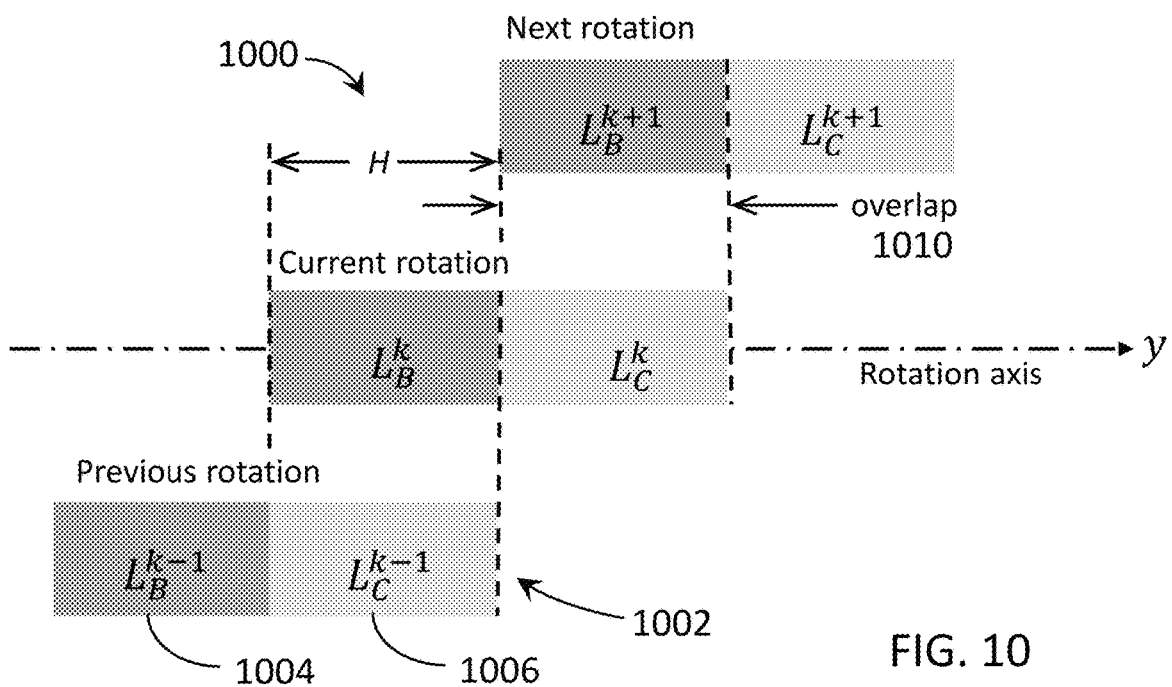
FIG. 10 shows schematic views of another exemplary detector with a one-sided shadow region during successive rotations of a scan.

FIGS. 9-10 show schematic views of exemplary detectors during scan geometries with a one-sided shadow zone. In the single-sided shadow case, only one side of the detector (in the axial direction) is used for scatter estimation. For example, in FIGS. 9-10, the back shadow region is used. However, the description below can be similarly applied to the case where the front shadow region is used for scatter measurement.

As mentioned above, the following notation is used to identify the detector regions: let $L_B^k$ and $L_C^k$ be the axial length of the back shadow region and the central region of the detector at the isocenter for the kth rotation, respectively; and let H be the traveled distance along the axial direction per rotation of the helical or step-and-shoot scans.

In this case, it is recommended that axial distance traveled per rotation, H, satisfies the following condition to make sure data for scatter estimation are available:

$$H<(L_C+L_B) \quad (3)$$

Like the two-sided case, if H satisfies this condition, there will be measured scatter from the neighboring rotation (back) that can directly contribute to the scatter estimation of the current projection.

For example, FIG. 9 shows schematic views of an exemplary detector 902 during scan geometry 900 with a one-sided shadow region during successive rotations of a scan. In particular, detector 902 includes a back shadow region 904 with axial length $L_B$ and central (primary) region 906 with axial length $L_C$. The detector 902 is shown with views during three successive rotations, where k is the current rotation, k−1 is the previous rotation, and k+1 is the next rotation.

As shown in FIG. 9, $H<L_C+L_B$, satisfying condition (3) above. If condition (3) is satisfied, the back shadow region 904 from a neighboring rotation (k+1) will overlap coverage with the central region 906 during the current rotation (k). Here, a portion of the back shadow region 904 from the next rotation (k+1) overlaps with the central region 906 during the current rotation (k), shown as overlap 910. The scatter measurements from this shadow region 904 can be used for estimating the scatter in the measured projection data in the central region 906, as described above.

Assuming that H satisfies the above condition (3), scatter measurements from neighboring rotations that overlap with the current measured projection data can be used to estimate the scatter of the current view.

An exemplary optimized balance between scan speed and scatter estimation accuracy can be defined by the following condition:

$$H=L_C=L_B \quad (4)$$

For example, FIG. 10 shows schematic views of an exemplary detector 1002 during scan geometry 1000 with a one-sided shadow region during successive rotations of a scan. In particular, detector 1002 includes a back shadow region 1004 with axial length $L_B$ and central (primary) region 1006 with axial length $L_C$. The detector 1002 is shown with views during three successive rotations, where k is the current rotation, k−1 is the previous rotation, and k+1 is the next rotation.

As shown in FIG. 10, $H=L_C=L_B$, satisfying condition (4) above. If condition (4) is satisfied, the shadow region 1004 (next) from a neighboring rotation (k+1) will completely overlap coverage with the central region 1006 during the current rotation (k). In particular, the back shadow region 1004 from the next rotation (k+1) overlaps with the central region 1006 during the current rotation (k), shown as overlap 1010. The scatter measurements from this shadow region 1004 can be used for estimating the scatter in the measured projection data in the central region 1006, as described above. Overlap area 1010 provides complete coverage for central region 1006, since $L_C=L_B$, which results in high accuracy of the scatter estimation. In addition, since $H=L_C$, the scan geometry optimizes speed by not overlapping the central region in successive rotations.

In the above embodiments, for helical and step-and-shoot scans, the central (primary) detector region used for projection measurements, as created by the beamformer, is rectangular. However, the beamformer can create and adjust the beam into various other window shapes. For example, for a fixed-pitch helical scan, exact image reconstruction can be achieved by using projection data located within the Tam-Danielson window. For helical scans that do not require variable pitch, the beamformer can be designed to match the Tam-Danielson window, and the detector areas outside of the Tam-Danielson window can be used for scatter measurement.

Figure 11:
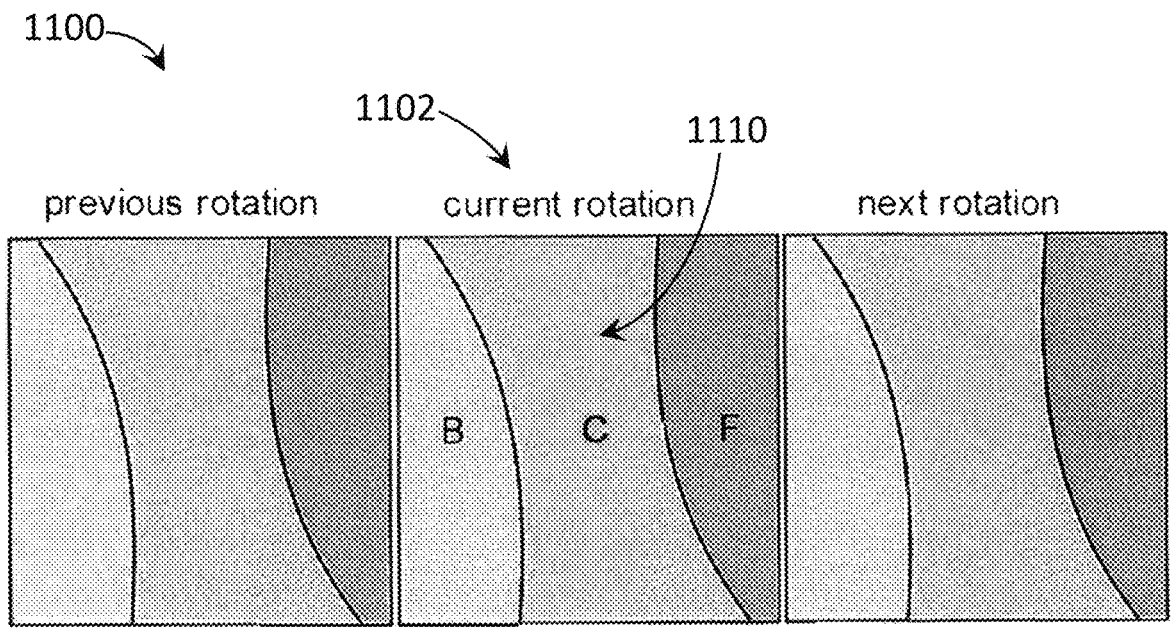
FIG. 11 shows an exemplary view with a Tam-Danielson window projected onto a detector.

For example, FIG. 11 shows an exemplary view 1100 with a Tam-Danielson window 1110 projected onto a detector 1102. In particular, detector 1102 includes a back (B) shadow region, a central (C) region, and a front (F) shadow region. The detector 1102 is shown with views showing the Tam-Danielson window 1110 during three successive rotations. The central (C) region of projection measurements is bounded by the Tam-Danielson window 1110. The back (B) and front (F) shadow regions are blocked from direct radiation by the beamformer and can be used for scatter estimation, as described above. Utilization of this window allows exact image reconstruction with excellent dose efficiency and increase scan speed.

However, view/design 1100 is limited by helical pitch, because it is applicable to only one scan geometry configuration. To improve flexibility, the beamformer's collimation window can be designed to be a parallelogram that is shaped based on the Tam-Danielson window. Such a collimation window will still provide sufficient projection data for exact image reconstruction, similar dose efficiency, and yet more collimation window options.

Figure 12:
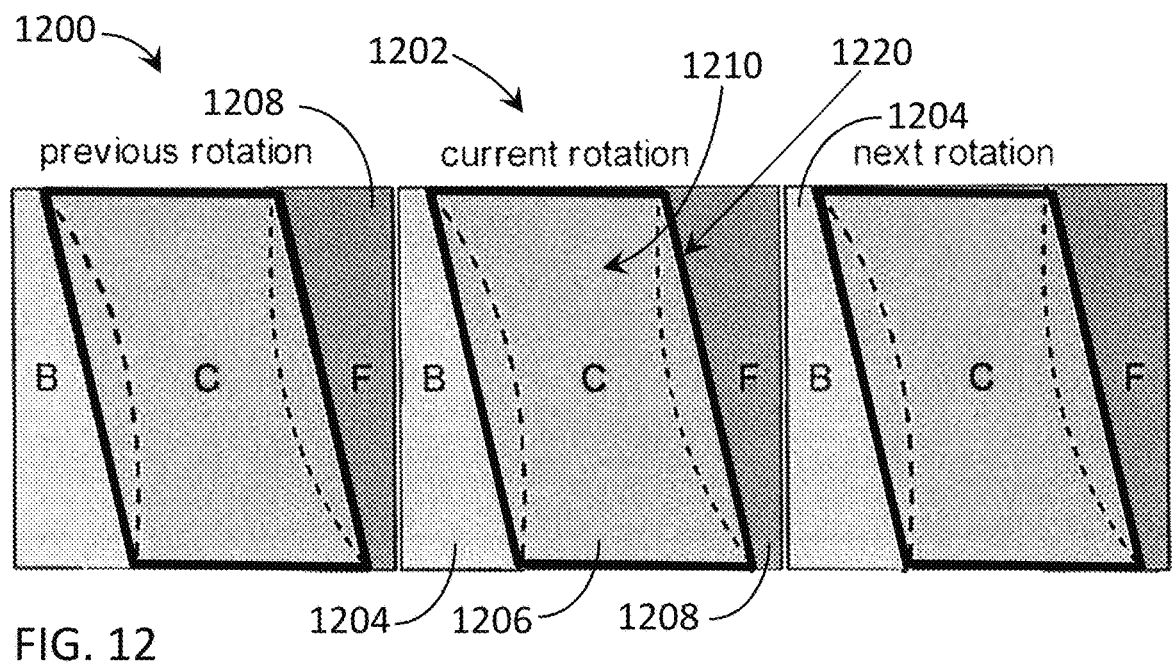
FIG. 12 shows an exemplary view with a Tam-Danielson window projected onto a detector with a beamformer parallelogram.

For example, FIG. 12 shows an exemplary view 1200 with a Tam-Danielson window 1210 projected onto a detector 1202. In this embodiment, a parallelogram 1220 shaped by the beamformer is shown surrounding the Tam-Danielson window 1210 (dashed lines) projected onto the detector 1202. Based on this parallelogram shape 1220, the detector 1210 includes a back (B) shadow region 1204, a central (C) region 1206 within the parallelogram 1220, and a front (F) shadow region 1208. The detector 1202 is shown with views showing the Tam-Danielson window 1210 bounded by parallelogram 1220 during three successive rotations. The central (C) region 1206 projection measurements contain the Tam-Danielson window 1210. The back (B) and front (F) shadow regions 1204, 1208 are blocked from direct radiation by the beamformer and can be used for scatter estimation, as described above. The parallelogram collimation window 1220 is not limited to one helical pitch, as it can be achieved by an appropriate beamformer design to accommodate different helical pitch and scan needs.

In some embodiments, the back-shadow region 1204 of the current rotation can be combined with the front-shadow region 1208 of the previous rotation to form an extended back-shadow scatter measurement region. Similarly, the front-shadow region 1208 of the current rotation can be combined with the back-shadow region 1204 of the next rotation to form an extended front-shadow scatter measurement region. In this manner, scatter in the central region 1206 of the current rotation can be interpolated using extended scatter measurements on one or both sides of the current rotation.

As shown in FIG. 12, the front and back shadow regions 1204, 1208, even when extended, do not have coverage overlap with the central region 1206. However, to improve the estimation accuracy and stability, direct scatter measurements from the neighboring rotations can be used for the scatter estimation of the current rotation. In other words, a scan can be designed so that coverage of the scatter measurements and the projection measurements overlap (direct scatter measurement availability).

Figure 13:
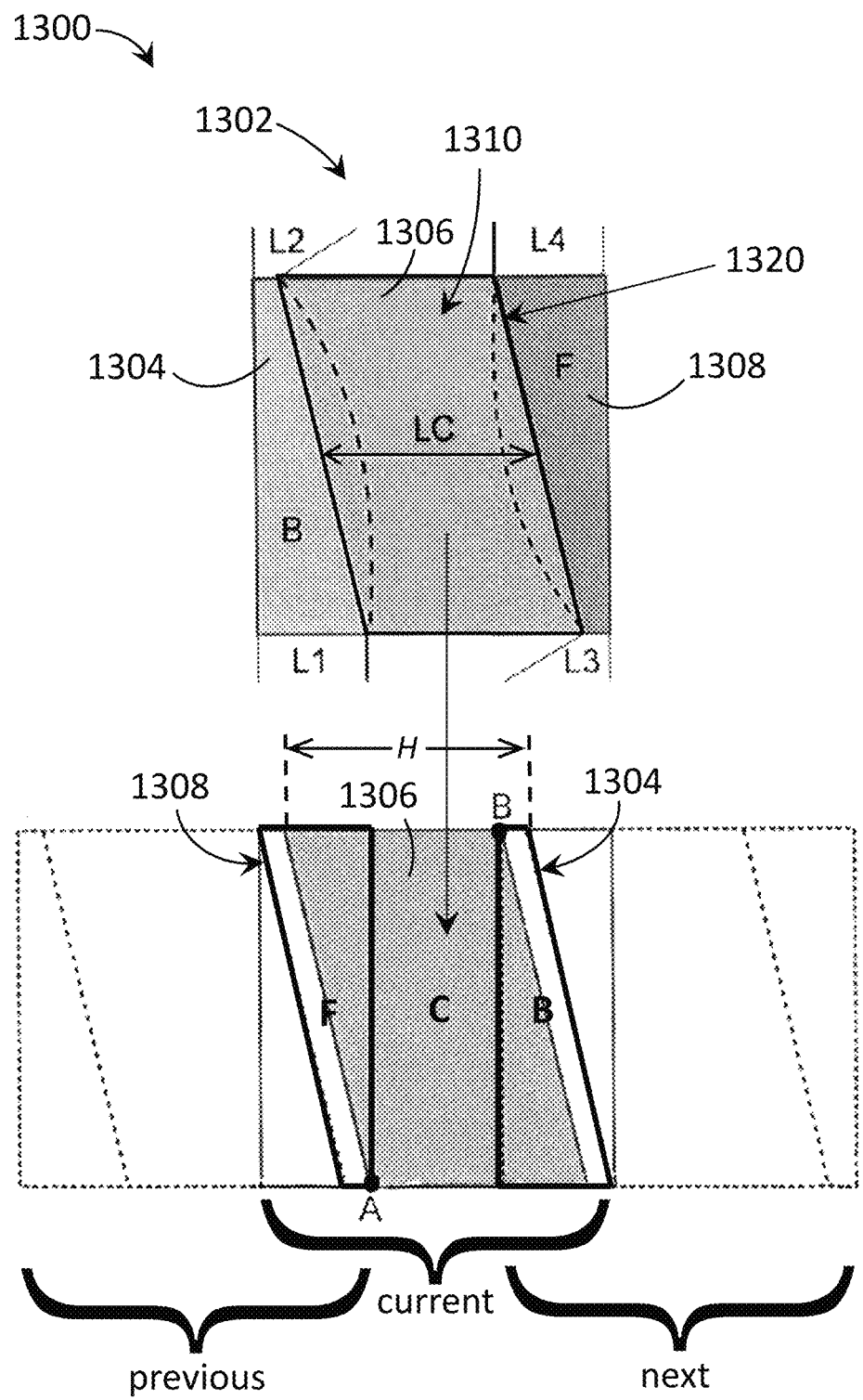
FIG. 13 shows an exemplary view with a Tam-Danielson window projected onto a detector with a beamformer parallelogram and shadow regions.

For example, FIG. 13 shows an exemplary view 1300 with a Tam-Danielson window 1310 projected onto a detector 1302. In this embodiment, a parallelogram 1320 shaped by the beamformer is shown surrounding the Tam-Danielson window 1310 (dashed lines) projected onto the detector 1302. Let $L_C$ (shown as LC in FIG. 13) be the axial length of the central region 1306 of the detector for projection acquirement (at the iso-center, which is the same for the subsequent axial length definitions). Let $L_{1,2,3,4}$ (shown as L1 L2, L3, and L4) be the axial lengths defining the trapezoid shapes of the back (B) and front (F) shadow regions 1304, 1308 of the detector as shown in the top of FIG. 13 during the same rotation. In this embodiment, the design can be achieved with the following condition:

$$\begin{cases} H < \max(L_2, L_3) + L_C \\ L_{1,2,3,4} \geq 0 \end{cases} \quad (5)$$

To satisfy the direct scatter measurement availability requirement, H must satisfy condition (5). The two points A and B shown in the lower portion of FIG. 13 are crucial for understanding equation (5). In particular, at least one of these points A, B should be viewable from the shadow regions of the neighboring rotations. In this manner, as shown in the lower portion of FIG. 13, center (C) region 1306 of the current rotation is overlapped by a front (F) shadow region 1308 from the previous rotation and a back (B) shadow region 1304 from the next rotation, where condition (5) is satisfied, which captures both points A and B in this two-sided embodiment.

Assuming that H satisfies the above condition (5), scatter measurements from neighboring rotations that overlap with the current measured projection data can be used to estimate the scatter of the current view.

An exemplary optimized balance between scan speed and scatter estimation accuracy can be defined by the following conditions:

$$\begin{cases} L_1 = L_4 \\ L_2 = L_3 \\ L_C = L_1 + L_3 \\ H = L_C \end{cases} \quad (6)$$

Figure 14:
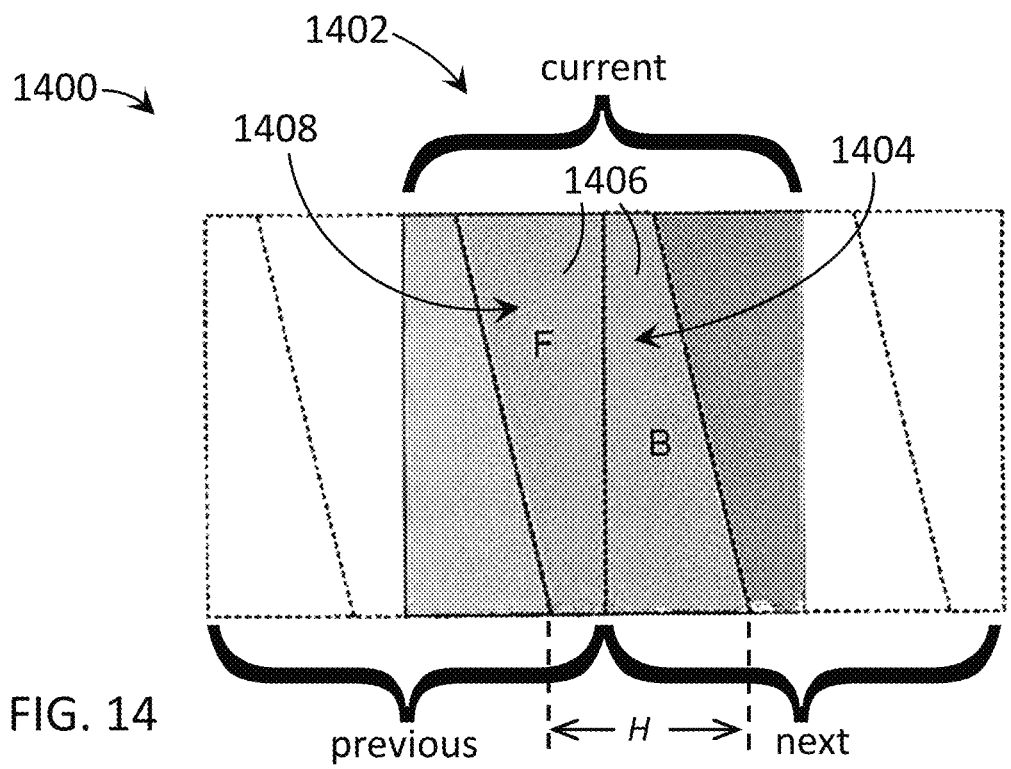
FIG. 14 shows schematic views of an exemplary detector with a two-sided shadow region during successive rotations of a scan.

For example, FIG. 14 shows schematic views of an exemplary detector 1402 during scan geometry 1400 with a two-sided shadow region during successive rotations of a scan. This design is a specific embodiment of the design shown in FIG. 13 that satisfies condition (6). In particular, detector 1402 includes a back (B) shadow region 1404, a central (primary) region 1406, and a front (F) shadow region 1408. The detector 1402 is shown with views during three successive rotations where center region 1406 of the current rotation is completely overlapped by a front (F) shadow region 1408 from the previous rotation and a back (B) shadow region 1404 from the next rotation. The scatter measurements from these shadow regions 1404, 1408 can be fully available for estimating the scatter in the measured projection data in the central region 1406, as described above. The overlap area provides complete coverage for central region 1406, since $H = L_C$ and the dimensions of the trapezoids formed by $L_{1,2,3,4}$ result in matching of the shapes of the combined shadow regions 1404, 1408 with the primary region 1406, which results in high accuracy of the scatter estimation. In addition, the scan geometry optimizes speed by not overlapping the central region in successive rotations.

It is important to note that off-centered detector in the transverse direction is allowed in all cases described above.

Figure 15:
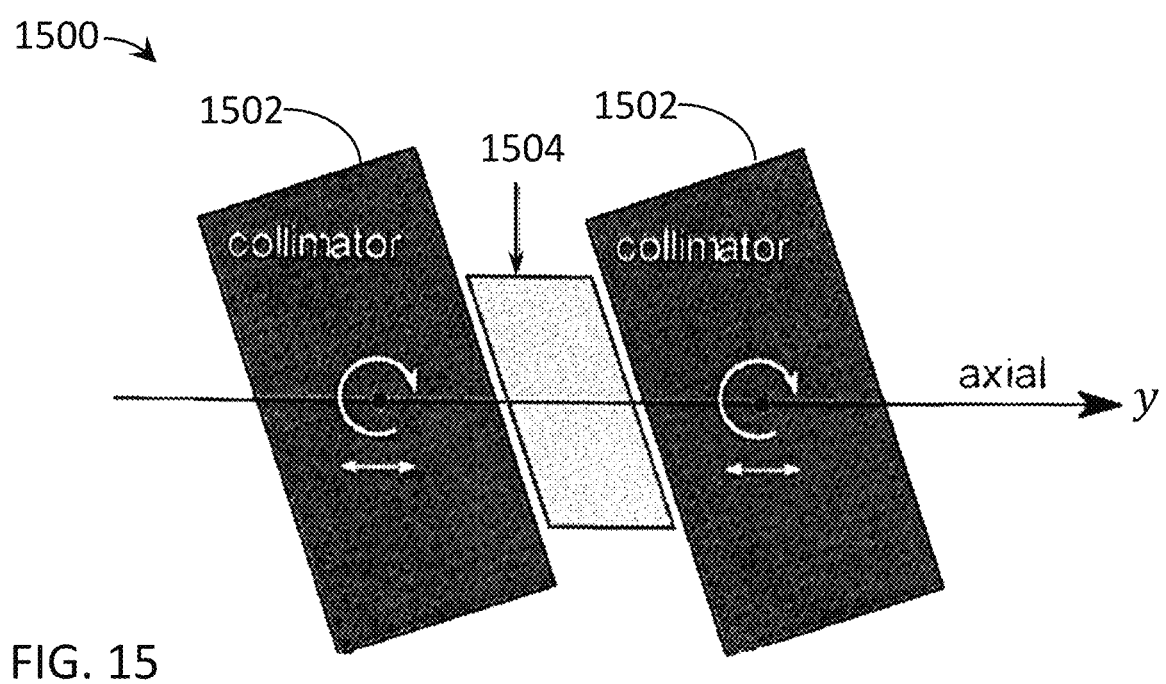
FIG. 15 illustrates an exemplary beamformer design with a collimator configured to adjust the shape of the radiation beam into a parallelogram shape.

FIG. 15 illustrates an exemplary beamformer configuration/design 1500 with collimator portions 1502 capable of being configured to adjust the shape of the radiation beam into a parallelogram shape 1504 matching the desired windows associated with the embodiments described above. The collimator/beamformer 1502 (which may be, e.g., beamformer 36) can be made of high x-ray attenuated material, such as tungsten. Beamformer/collimator 1502 can be rotated and translated (shifted in the longitudinal direction along the y-axis) to adjust the shape of the desired window 1504 within a range to meet the requirements of various applications, including with offset detectors.

To make the scatter estimation more accurate, the penumbra region of the beamformer should be excluded. In one embodiment, this can be achieved by automatically detecting the axial profile of each projection and then excluding a number of predefined pixels in the axial direction. Another method is to perform an experiment ahead of time for different window and scan configurations and predefine the back and front regions for scatter measurement in view of the penumbra area.

The following flow charts and block diagrams illustrate exemplary configurations and methodologies associated with scatter estimation in accordance with the systems described above. The exemplary methodologies may be carried out in logic, software, hardware, or combinations thereof. In addition, although the procedures and methods are presented in an order, the blocks may be performed in different orders, including series and/or parallel. Thus, the steps below, including imaging, image-based pre-delivery steps, and treatment delivery, although shown sequentially, may be executed simultaneously, including in real-time. Further, additional steps or fewer steps may be used.

Figure 16:
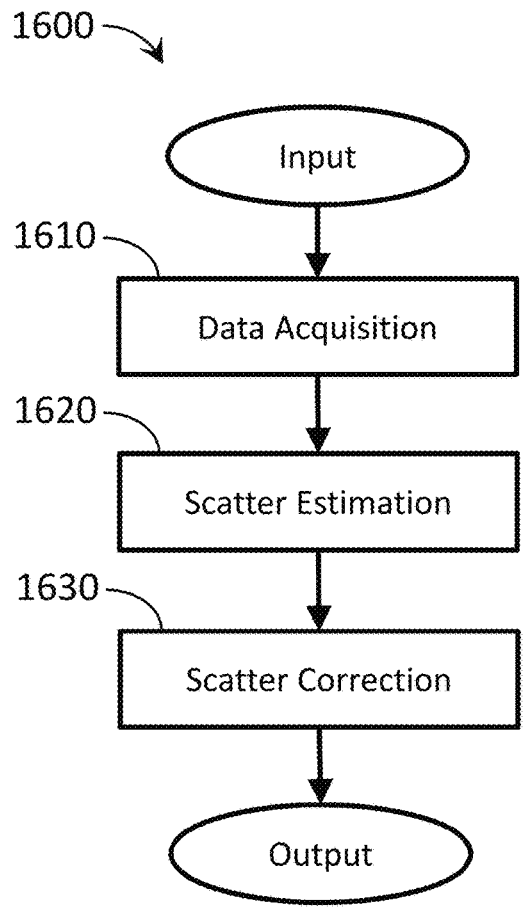
FIG. 16 is a flow chart depicting an exemplary method of scatter correction.

FIG. 16 is a flow chart depicting an exemplary method 1600 of scatter correction using a scan design, such as those described above. Inputs can include any optional prior data and/or scan designs. In this embodiment, step 1610 includes data acquisition. For example, during successive rotations of a radiation source projecting a collimated radiation beam towards a target and radiation detector, the method measures projection data (primary+scatter) in a central (primary) region of a radiation detector and measures scatter using a front shadow peripheral region and/or a back shadow peripheral region of the detector, in accordance with any of the embodiments described above.

Data acquisition in step 1610 can also include adjusting a shape of the radiation beam with the beamformer during the scan. Adjusting the shape of the radiation beam with the beamformer can include rotation and translation of highly x-ray attenuated material of the beamformer during the scan to block radiation from directly exposing shadow regions. In one embodiment, the method includes adjusting a shape of the radiation beam with a beamformer to be a rectangle associated with a scan design, including for a helical or a step-and-shoot circular scan. In another embodiment, the method includes adjusting a shape of the radiation beam with a beamformer to be a parallelogram containing a Tam-Danielson Window associated with a pitch of a helical scan. The beamformer can adjust the shape of the radiation beam based on a longitudinal distance between rotations of the x-ray source, including embodiments where the longitudinal distance is a step distance between successive circular scans and embodiments where the longitudinal distance is a pitch during a helical scan. In some embodiments the step or the pitch varies during the scan and the beamformer can adjust the beam shape accordingly.

Next, step 1620 includes scatter estimation. For example, for each rotation, the method estimates the scatter in the projection data from the central (primary) region using the scatter measurement from the current rotation and/or the scatter measurement of the neighboring rotations at the same azimuth angle, in accordance with any of the embodiments described above. Then, step 1630 includes scatter correction. For example, scatter estimated from step 1620 is subtracted from the projection data to obtain scatter corrected projection data. Output includes scatter corrected projection data suitable for imaging. Various embodiments can utilize different scan geometries, detector positioning, and/or beamformer window shapes. As mentioned above, the detector may also be offset in the transverse direction.

Figure 17:
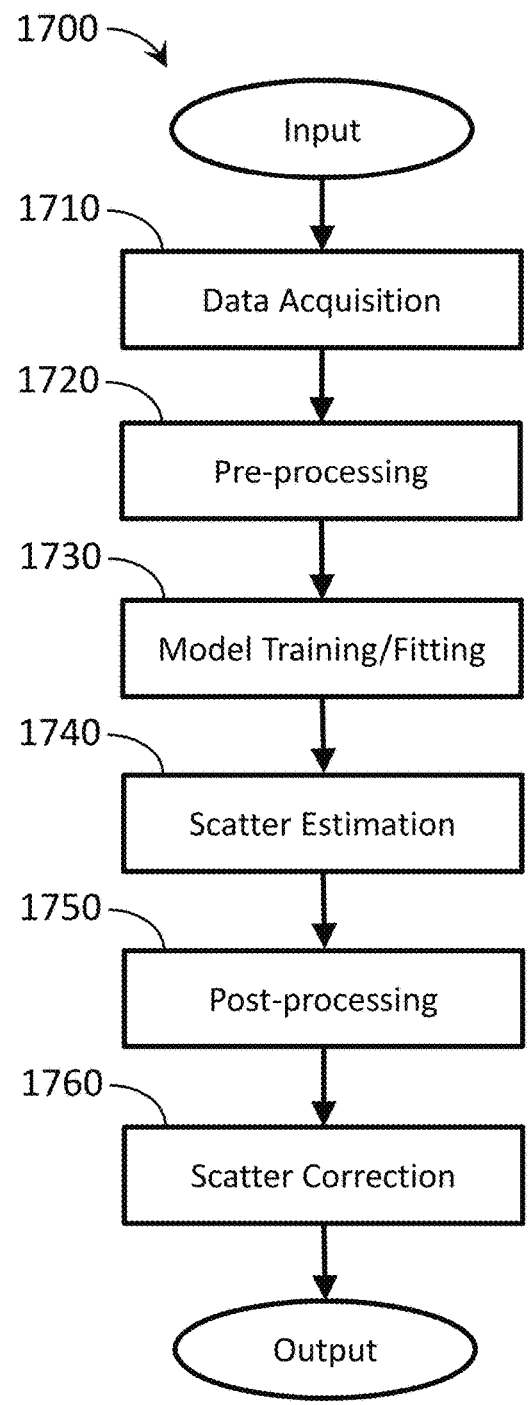
FIG. 17 is a flow chart depicting another exemplary method of scatter correction.

One or more optimization processes are also applicable to all of the above embodiments to estimate scatter. For example, FIG. 17 is a flow chart depicting an exemplary method 1700 of scatter correction using a scan design, such as those described above. Inputs can include any optional prior data and/or scan designs. In this embodiment, step 1710 includes data acquisition, where the method measures projection data in a central (primary) region of a radiation detector and measures scatter in shadowed peripheral region (s) of the detector, including required adjustments by the beamformer as discussed above. Next, at step 1720, the data acquired can be pre-processed. For example, pre-processing can include smoothing the scatter measurements. In another example, pre-processing can include finding relations between the scatter measurements of the current rotation and the neighboring rotations to modify the neighboring measurements to improve estimation accuracy. Then, at step 1730, the method can utilize various model training/fitting techniques to optimize the measured scatter data based on an optimization model, including distinguishing data quality/importance from different locations. A detailed example is included in the method described below.

Next, step 1740 includes scatter estimation, where the method estimates the scatter in the projection data from the central (primary) region using both the scatter measurements of the current rotation and that of the neighboring rotations, for each rotation. Next, step 1750 can include post-processing the estimated scatter. For example, post-processing can include applying a filtering process across channels and/or views to improve scatter smoothness. Then, step 1760 includes scatter correction, where the method subtracts the estimated scatter from the projection data to obtain scatter corrected projection data. Like the steps of method 1600, steps of method 1700 can be implemented in accordance with any of the embodiments described above. Output includes scatter corrected projection data suitable for imaging. Various embodiments can utilize different scan geometries, detector positioning (including offset detectors), and/or beamformer window shapes.

Figure 18:
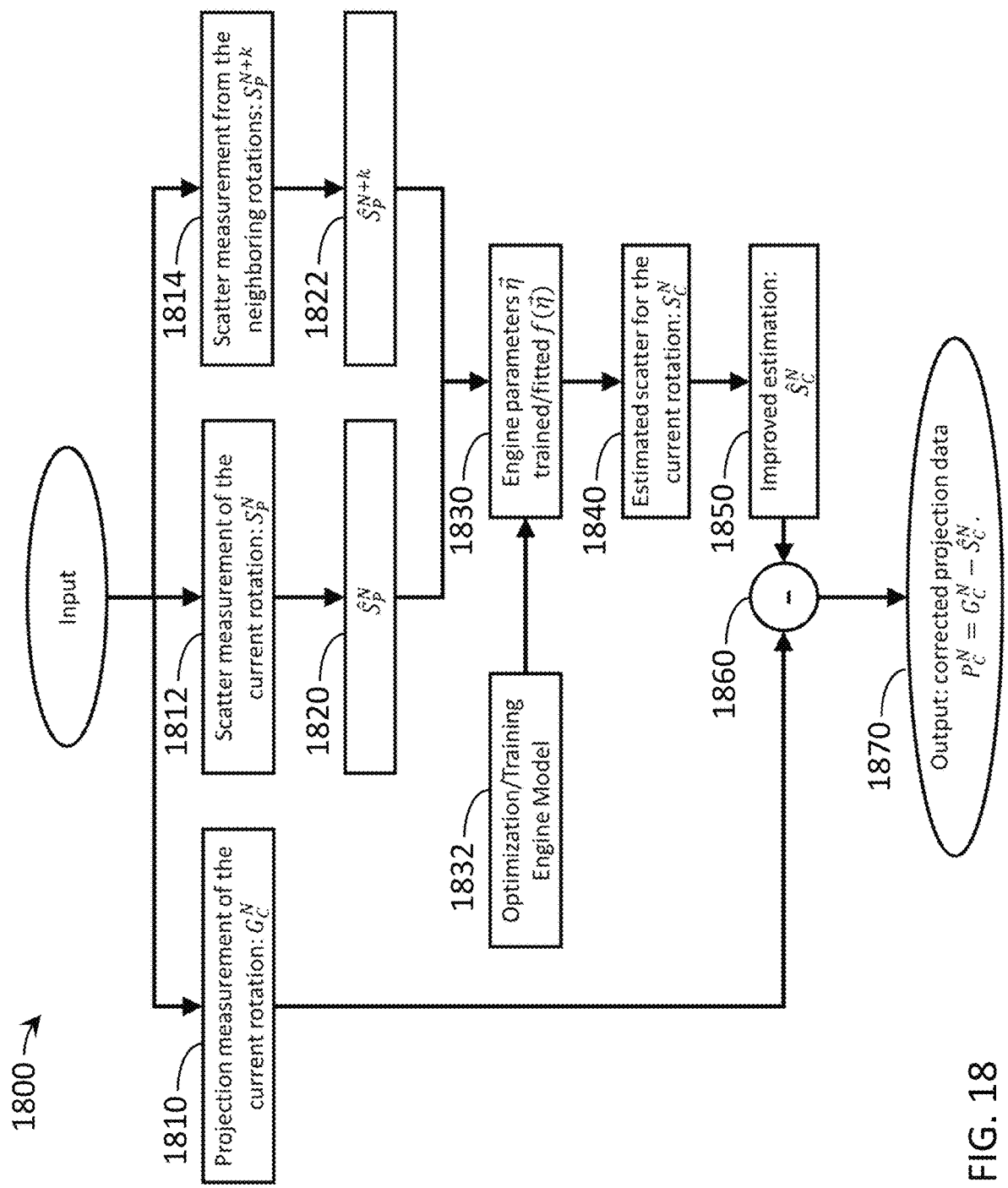
FIG. 18 is a flow chart depicting an exemplary method of optimized scatter correction.

In another embodiment, FIG. 18 is a flow chart depicting an exemplary method 1800 of optimized scatter correction using a scan design, such as those described above. Inputs can include any optional prior data and/or scan designs. FIG. 18 depicts a high-level diagram of the workflow (framework) for the optimized scatter correction. For convenience, the following notation is utilized:

$G_C^N$: measured projection data in the central region of the detector for the Nth rotation $S_P^N$: measured scatter in the peripheral (shadowed) region of the detector for the Nth rotation $\hat{S}_P^N$: pre-processed $S_P^N$ $f(\vec{\eta})$: f is the fitting/training model and $\vec{\eta}$ is a vectoral parameter of the model $S_C^N$: estimated scatter in the central region of the detector for the Nth rotation $\hat{S}_C^N$: post-processed $S_C^N$ $P_C^N$: corrected projection data (primary) in the central region of the detector for the Nth rotation In this embodiment, steps 1810, 1812, 1814 include data acquisition. Step 1810 includes projection measurement of the current rotation. Step 1812 includes scatter measurement of the current rotation. Step 1814 includes scatter measurement from the neighboring rotations (e.g., next rotation k+1 in a one-sided embodiment). Next, at steps 1820, 1822, the scatter measurements can be pre-processed (e.g., smoothing the scatter measurements, finding relations between the scatter measurements of the current rotation and the neighboring rotations to modify the neighboring measurements to improve estimation accuracy, etc.). Then, at step 1830, the method can utilize an optimization/training engine model 1832 such that engine parameters $\vec{\eta}$ are trained/fitted in accordance with an optimization function $f(\vec{\eta})$. In this embodiment, the goal is to find the best fitting parameter set $\vec{\eta}*$. Various optimization methods may be applied in this context.

Next, step 1840 estimates scatter for the current rotation, in accordance with any of the embodiments described above. Next, step 1850 can improve the estimated scatter via post-processing (e.g., applying a filtering process across channels and/or views to improve scatter smoothness, etc.). Then, step 1860 includes subtracting the estimated scatter for the current rotation from the projection measurement of the current rotation to obtain corrected projection data, output at step 1870. As mentioned above, various steps, including, for example, steps 1820, 1822, 1850, may not be utilized, depending on the application. Various embodiments can utilize different scan geometries, detector positioning (including offset detectors), and/or beamformer window shapes.

In this manner, various embodiments of the systems and methods estimate scatter of the current rotation by using measured scatter outside the collimation opening (in the longitudinal direction) of the current view and measured scatter from the longitudinally shifted views (but with the same azimuth angle) in neighboring scan rotation(s). Scan designs can be optimized to balance scan speed and scatter estimation accuracy. The systems and methods are applicable to various scans, including, for example, both helical scans and step-and-shoot scans. In various embodiments, the detector signal measured in the regions outside of the beamformer opening (shadow regions) is assumed to be entirely attributable to scatter. The scatter may be composed only of Compton scatter, with no or very minimal Rayleigh scatter unless the axial collimation width is very narrow. The systems and methods can be robust, fast, convenient, and/or dose efficient. Various embodiments of the systems and methods do not require prior information of the data acquisition system or patient information. Embodiments do not require extra equipment such as beam blockers.

When compared to the shadow method of estimating scatter, various embodiments of the above systems and methods can exhibit various advantages: more accurate, using more direct measurement, especially in situations where the scanned object is heterogenic in the axial direction, e.g., the head, neck and shoulder regions; enables scatter correction using only one side of the detector outside the beamformer opening; enables scatter correction for axially long objects scanned using helical or step-and-shoot trajectories; and/or provides options for optimized data acquisition and dose usage for image reconstruction.

As is discussed above, aspects of the disclosed technology can be utilized in a radiotherapy device and method that make use of integrated kV CT for use in conjunction with or as part of IGRT. In accordance with one embodiment, the image acquisition methodology includes or otherwise makes use of a helical source trajectory (e.g., a continuous source rotation about a central axis together with longitudinal movement of a patient support through a gantry bore) with a kV beam collimation, together with fast slip ring rotation, to provide kV CT imaging on a radiation therapy delivery platform. It will be appreciated that such an implementation can provide reduced scatter and improved scatter estimation to enable kV images of higher quality than conventional systems.

It will be further appreciated that any potential increased scan time associated with multiple beam rotations to complete a volume image can be mitigated or otherwise offset by high kV frame rates, high gantry rates, and/or sparse data reconstruction techniques. It will be further appreciated that the above-described provision of a selectively controllable collimator/beamformer allows for a system where a user can trade off or otherwise vary image acquisition time versus image quality, depending on the specific application and/or clinical need. It also will be appreciated that the radiotherapy delivery device can be controlled to provide half- or single-rotation CBCT scans (with potential reduced image quality due to scatter) with fast image acquisition time (e.g., for motion tracking), as well as continuous helical acquisition with a narrow/slit fan beam with longer acquisition time, but increased image quality due to reduced scatter.

Figure 19:
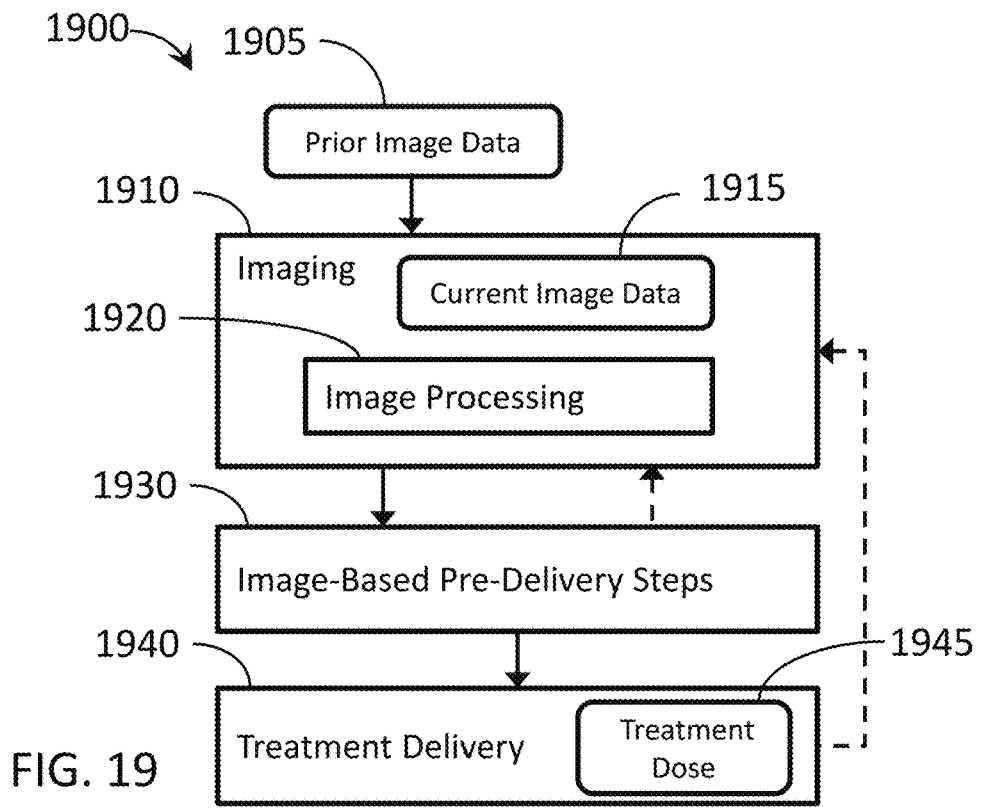
FIG. 19 is a flow chart depicting an exemplary method of IGRT using a radiotherapy device.

FIG. 19 is a flow chart depicting an exemplary method 1900 of IGRT using a radiotherapy device (including, e.g., x-ray imaging apparatus 10). Prior image data 1905 of the patient may be available for use, which may be a previously-acquired planning image, including a prior CT image. Prior data 1905 can also include treatment plans, phantom information, models, a priori information, etc. In some embodiments, prior image data 1905 is generated by the same radiotherapy device, but at an earlier time. At step 1910, imaging of a patient is performed using a source of low-energy radiation (e.g., kV radiation from x-ray source 30). In one embodiment, imaging comprises a helical scan with a fan or cone beam geometry. Step 1910 can produce high-quality (HQ) image(s) or imaging data 1915 using the scatter estimation and correction techniques described above. In some embodiments, image quality may be adjusted to optimize a balance between image quality/resolution and dosage. In other words, not all images need to be of the highest quality or image quality may be adjusted to optimize or trade off a balance between image quality/resolution and image acquisition time. Imaging step 1910 can also include image processing to generate patient images based on the imaging data (e.g., in accordance with the methods described above). Although image processing step 1920 is shown as part of imaging step 1910, in some embodiments image processing step 1920 is a separate step, including where image processing is executed by separate devices.

Next, at step 1930, one or more image-based pre-delivery steps, discussed below, are performed based at least in part on the imaging data 1915 from step 1910. As discussed in more detail below, step 1930 can include determining various parameters associated with the therapeutic treatment and (subsequent) imaging planning. In some embodiments, image-based pre-delivery steps (1930) may require more imaging (1910) before treatment delivery (1940). Step 1930 can include adapting a treatment plan based on the imaging data 1915 as part of an adaptive radiotherapy routine. In some embodiments, image-based pre-delivery steps 1930 may include real-time treatment planning. Embodiments may also include simultaneous, overlapping, and/or alternating activation of the imaging and therapeutic radiation sources. Real-time treatment planning may involve any or all of these types of imaging and therapeutic radiation activation techniques (simultaneous, overlapping, and/or alternating).

Next, at step 1940, therapeutic treatment delivery is performed using a source of high-energy radiation (e.g., MV radiation from therapeutic radiation source 20). Step 1940 delivers a treatment dose 1945 to the patient according to the treatment plan. In some embodiments, the IGRT method 1900 may include returning to step 1910 for additional imaging at various intervals, followed by image-based pre-delivery steps (1930) and/or treatment delivery (1940) as required. In this manner the high-quality imaging data 1915 may be produced and utilized during IGRT using one apparatus 10 that is capable of adaptive therapy. As mentioned above, steps 1910, 1920, 1930, and/or 1940 may be executed simultaneously, overlapping, and/or alternating.

IGRT can include at least two general goals: (i) to deliver a highly conformal dose distribution to the target volume; and (ii) to deliver treatment beams with high accuracy throughout every treatment fraction. A third goal can be to accomplish the two general goals in as little time per fraction as possible. Delivering treatment beams accurately requires the ability to identify and/or track the location of the target volume intrafraction with high-quality images. The ability to increase delivery speed requires the ability to accurately, precisely, and quickly move the radiation source according to the treatment plan.

Figure 20:
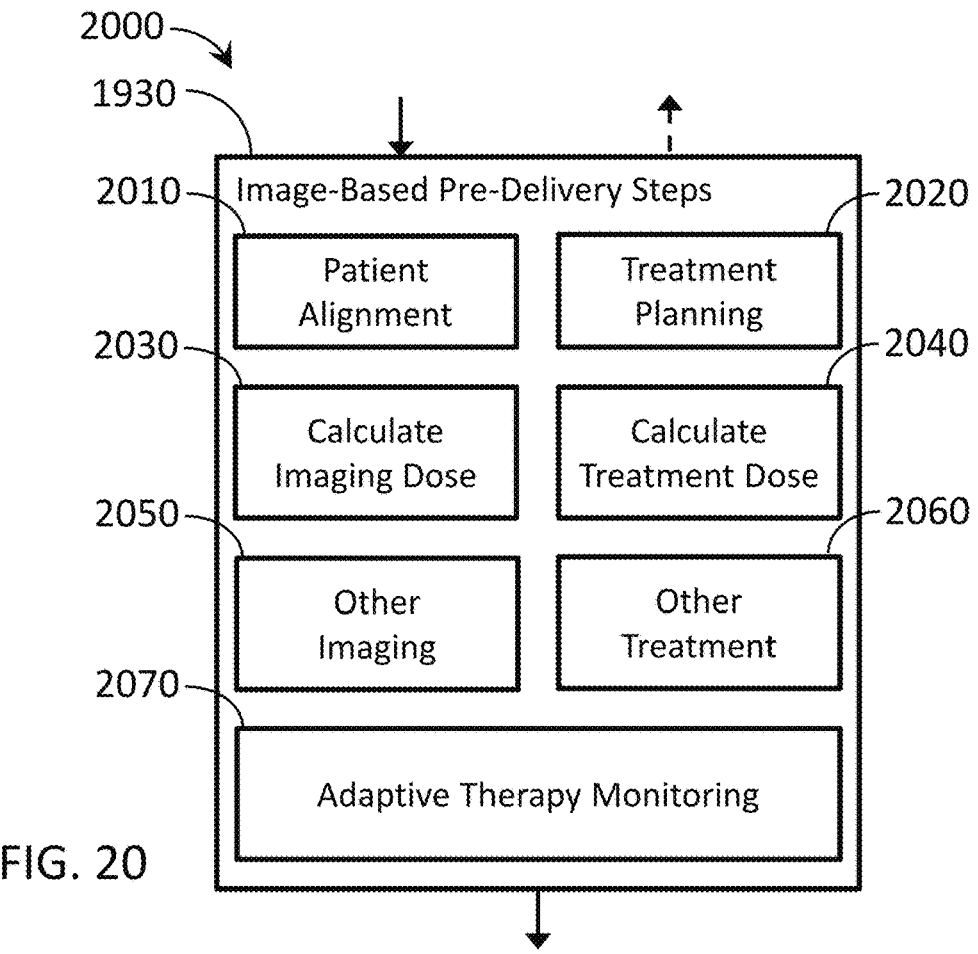
FIG. 20 is a block diagram depicting exemplary image-based pre-delivery steps.

FIG. 20 is a block diagram 2000 depicting exemplary image-based pre-delivery steps/options that may be associated with step 1930 above. It will be appreciated that the above-described x-ray imaging apparatus 10 (e.g., as part of a radiotherapy device) can generate kV images that can be used in a variety of ways, including for image-based pre-delivery steps (1930), without departing from the scope of the present invention. For example, images 1915 generated by the radiotherapy device can be used to align a patient prior to treatment (2010). Patient alignment can include correlating or registering the current imaging data 1915 with imaging data associated with earlier pre-treatment scans and/or plans, including the treatment plan. Patient alignment can also include feedback on the physical position of the patient relative to the radiation source to verify whether the patient is physically within the range of the delivery system. If necessary, the patient can be adjusted accordingly. In some embodiments, patient alignment imaging may purposely be of lesser quality to minimize dosage but provide adequate alignment information.

Images generated by the x-ray imaging apparatus 10 can also be used for treatment planning or re-planning (2020). In various embodiments, step 2020 can include confirming the treatment plan, modifying the treatment plan, generating a new treatment plan, and/or choosing a treatment plan from a set of treatment plans (sometimes referred to as "plan of the day"). For example, if the imaging data 1915 shows that the target volume or ROI is the same as when the treatment plan was developed, then the treatment plan can be confirmed. However, if the target volume or ROI is not the same, re-planning of the therapeutic treatment may be necessary. In the case of re-planning, because of the high quality of the imaging data 1915 (generated by the x-ray imaging apparatus 10 at step 1910), the imaging data 1915 may be used for treatment planning or re-planning (e.g., generating a new or modified treatment plan). In this manner, pre-treatment CT imaging via a different device is not necessary. In some embodiments, confirming and/or re-planning may be an ongoing procedure before and/or after various treatments.

In accordance with another exemplary use case, images generated by the x-ray imaging apparatus 10 can be used to calculate imaging dose (2030), which may be used for ongoing determinations of total dose to the patient and/or for subsequent imaging planning. The quality of subsequent imaging may also be determined as part of the treatment planning, for example, to balance quality and dosage. In accordance with another exemplary use case, images generated by the x-ray imaging apparatus 10 can be used to calculate treatment dose (2040), which may be used for ongoing determinations of total dose to the patient and/or may be included as part of treatment planning or re-planning.

In accordance with other exemplary use cases, images generated by the x-ray imaging apparatus 10 can be used in connection with planning or adjusting other imaging (2050) and/or other treatment (2060) parameters or plans, including, for example, as part of adaptive therapy and/or treatment plan generation. In accordance with another exemplary use case, images generated by the x-ray imaging apparatus 10 can be used in connection with adaptive therapy monitoring (2070), which can include monitoring treatment delivery and adapting as required.

It should be appreciated that the image-based pre-delivery steps (1930) are not mutually exclusive. For example, in various embodiments, calculate treatment dose (2040) can be a step by itself and/or can be part of adaptive therapy monitoring (2070) and/or treatment planning (2020). In various embodiments, the image-based pre-delivery steps (1930) can be performed automatically and/or manually with human involvement.

The devices and methods described above, including the adjustable collimation of the image radiation and the scatter estimation and correction schemes, provide improved scatter estimation, which results in kV-generated images of higher quality than conventional in-treatment imaging systems like CBCT.

Figure 21:
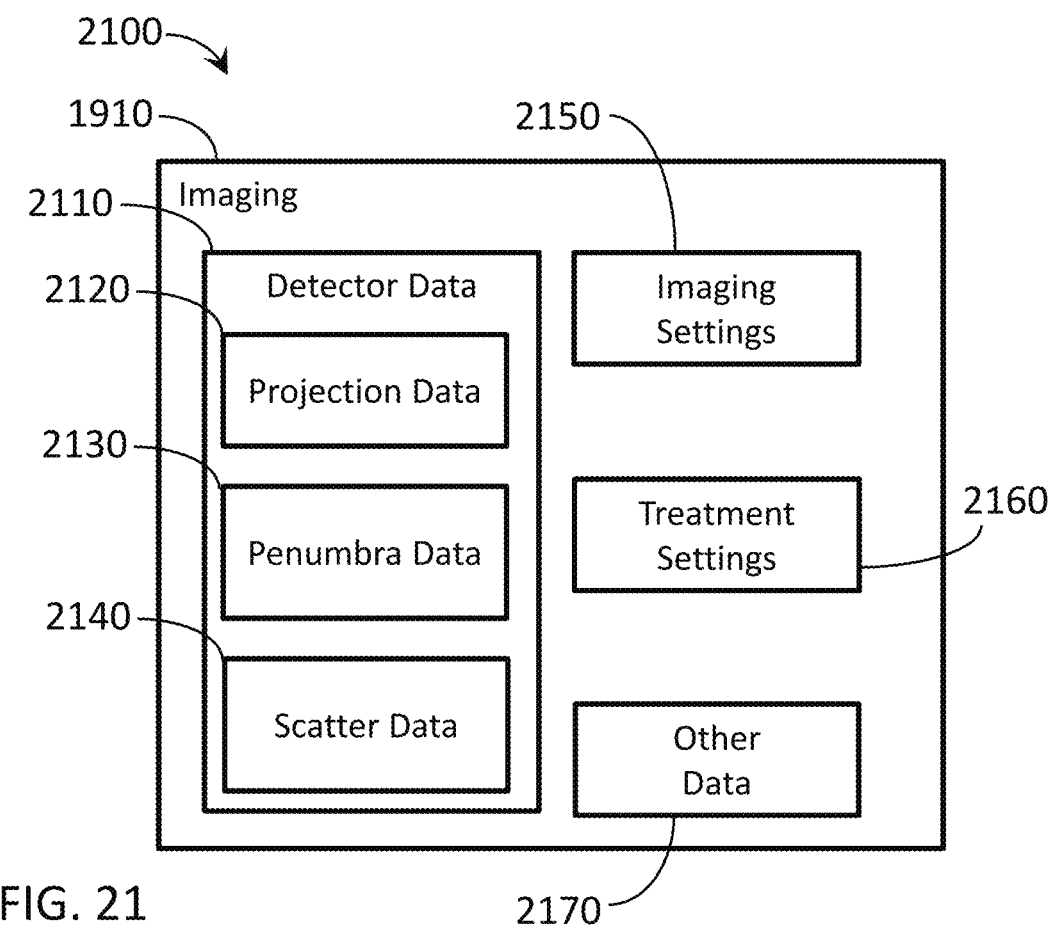
FIG. 21 is a block diagram depicting exemplary data sources that may be utilized during imaging or image-based pre-delivery steps.

FIG. 21 is a block diagram 2100 depicting exemplary data sources that may be utilized during imaging (1910) and/or subsequent image-based pre-delivery steps (1930). Detector data 2110 represents all of the data received by the image radiation detector 34. The projection data 2120 is the data generated by the radiation incident in the collimated beam area, referred to above as the primary or central region. The penumbra data 2130 is the data generated by the radiation incident in the penumbra area. The scatter data 2140 is the data generated by the radiation incident in the peripheral area outside of the penumbra area, referred to above as the shadow region(s).

In one embodiment, the penumbra data 2130 may be used to separate or identify the projection and/or scatter data. As described in detail above, the scatter data 2140 can be used to estimate the scatter radiation in the projection data 2120. In another embodiment, the scatter data 2140 can be used to determine the residual effect of the scatter from the therapeutic radiation source 20 (e.g., MV) when the two sources 20, 30 are operated simultaneously.

In this manner, the penumbra data 2130 and/or the scatter data 2140 may be utilized to improve the quality of the images generated by the imaging step 1910. In some embodiments, the penumbra data 2130 and/or the scatter data 2140 may be combined with the projection data 2120 and/or analyzed in view of the applicable imaging settings 2150, treatment settings 2160 (e.g., if simultaneous imaging and treatment radiation), and any other data 2170 associated with the x-ray imaging apparatus 10 at the time of the data collection at the imaging detector 34. In other embodiments, the data may be used for the treatment planning step 1930.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. An x-ray imaging apparatus, comprising:
a rotating x-ray source for emitting a radiation beam;
an x-ray detector positioned to receive radiation from the x-ray source;
a beamformer configured to adjust a shape of the radiation beam emitted by the x-ray source, such that a primary region of the x-ray detector is directly exposed to the radiation beam and at least one shadow region of the x-ray detector is blocked from direct exposure to the radiation beam by the beamformer;
a data processing system configured to:
receive measured projection data in the primary region and measured scatter data in the at least one shadow region; and
determine an estimated scatter in the primary region during a current rotation of the x-ray source based on the measured scatter data in the at least one shadow region during at least one of a previous rotation or a next rotation of the x-ray source;
wherein coverage of the at least one shadow region during at least one of the previous rotation or the next rotation overlaps the primary region during the current rotation at a common azimuth angle projecting onto a common plane.

2. The x-ray imaging apparatus of claim 1, wherein determining the estimated scatter in the primary region during the current rotation is further based on the measured scatter data in the at least one shadow region during the current rotation.

3. The x-ray imaging apparatus of claim 1, wherein the at least one shadow region of the x-ray detector comprises a back shadow region in a negative longitudinal direction from the primary region and a front shadow region in a positive longitudinal direction from the primary region.

4. The x-ray imaging apparatus of claim 3, wherein coverage of the front shadow region during the previous rotation and coverage of the back shadow region during the next rotation overlap the primary region during the current rotation, and wherein determining the estimated scatter in the primary region during the current rotation is based on the measured scatter data in the front shadow region during the previous rotation and the measured scatter data in the back shadow region during the next rotation.

5. The x-ray imaging apparatus of claim 4, wherein determining the estimated scatter in the primary region during the current rotation is further based on the measured scatter data in at least one shadow region during the current rotation.

6. The x-ray imaging apparatus of claim 1, wherein the beamformer adjusts the shape of the radiation beam based on a longitudinal distance between rotations of the x-ray source.

7. The x-ray imaging apparatus of claim 6, wherein the longitudinal distance is a step distance between successive circular scans.

8. The x-ray imaging apparatus of claim 6, wherein the longitudinal distance is a pitch during a helical scan, and wherein the shape of the radiation beam is a parallelogram configured to capture a Tam-Danielson Window associated with the pitch.

9. The x-ray imaging apparatus of claim 1, wherein the x-ray detector is offset in a transverse direction.

10. A method of estimating scatter in x-ray images, comprising:
receiving measured projection data from a primary region of an x-ray detector, wherein the primary region of the x-ray detector is directly exposed to a radiation beam from a radiation source during a scan;
receiving measured scatter data from at least one shadow region of the x-ray detector, wherein the at least one shadow region of the x-ray detector is blocked from direct exposure to the radiation beam; and
determining an estimated scatter in the measured projection data during a current rotation of the radiation source based on the measured scatter data in the at least one shadow region during at least one of a previous rotation or a next rotation of the radiation source;
wherein coverage of the at least one shadow region during at least one of the previous rotation or the next rotation overlaps the primary region during the current rotation of the radiation source at a common azimuth angle projecting onto a common plane.

11. The method of claim 10, wherein determining the estimated scatter in the measured projection data during the current rotation is further based on measured scatter data in the at least one shadow region during the current rotation.

12. The method of claim 10, wherein the at least one shadow region of the x-ray detector comprises a back shadow region and a front shadow region, and wherein coverage of the front shadow region during the previous rotation and coverage of the back shadow region during the next rotation overlap the primary region during the current rotation, and wherein determining the estimated scatter in the measured projection data during the current rotation is based on the measured scatter data in the front shadow region during the previous rotation and the measured scatter data in the back shadow region during the next rotation.

13. The method of claim 10, further comprising adjusting a shape of the radiation beam with a beamformer during the scan.

14. The method of claim 13, wherein adjusting the shape of the radiation beam with the beamformer comprises rotation and translation of x-ray attenuated material of the beamformer.

15. The method of claim 10, further comprising adjusting a shape of the radiation beam with a beamformer to be a rectangle associated with a step-and-shoot circular scan.

16. The method of claim 10, further comprising adjusting a shape of the radiation beam with a beamformer to be a parallelogram containing a Tam-Danielson Window associated with a pitch of a helical scan.

17. The method of claim 10, further comprising correcting the measured projection data based on the estimated scatter in the measured projection data.

18. The method of 10, further comprising optimizing the measured scatter data based on an optimization model.

19. The method of 10, further comprising optimizing a scan speed and a scatter estimation accuracy.

20. A radiotherapy delivery device comprising:
a rotatable gantry system positioned at least partially around a patient support;
a first source of radiation coupled to the rotatable gantry system, the first source of radiation being configured as a source of therapeutic radiation;
a second source of radiation coupled to the rotatable gantry system, the second source of radiation being configured as a source of imaging radiation having an energy level less than the source of therapeutic radiation;
a radiation detector coupled to the rotatable gantry system and positioned to receive radiation from the second source of radiation;

a beamformer configured to adjust a shape of a radiation beam emitted by the second source of radiation, such that a primary region of the radiation detector is directly exposed to the radiation beam and at least one shadow region of the radiation ray detector is blocked from direct exposure to the radiation beam by the beamformer; and a data processing system configured to:

receive measured projection data in the primary region and measured scatter data in the at least one shadow region; and determine an estimated scatter in the primary region during a current rotation of the second source of radiation based on the measured scatter data in the at least one shadow region during at least one of a previous rotation or a next rotation of the second source or radiation, wherein coverage of the at least one shadow region during at least one of the previous rotation or the next rotation overlaps the primary region during the current rotation at a common azimuth angle projecting onto a common plane;

reconstruct a patient image based on the estimated scatter; and deliver a dose of therapeutic radiation to the patient via the first radiation source based on the patient image during adaptive IGRT.

* * * * *